United States Patent
Zhu et al.

(10) Patent No.: US 11,974,383 B2
(45) Date of Patent: *Apr. 30, 2024

(54) SYSTEMS AND METHODS FOR FOCUS CONTROL IN X-RAYS

(71) Applicant: SHANGHAI UNITED IMAGING HEALTHCARE CO., LTD., Shanghai (CN)

(72) Inventors: Guoping Zhu, Shanghai (CN); Jinglin Wu, Shanghai (CN); Tieshan Zhang, Shanghai (CN); Siming Chen, Shanghai (CN); Xu Chu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 138 days.

This patent is subject to a terminal disclaimer.

(21) Appl. No.: 17/649,367

(22) Filed: Jan. 30, 2022

(65) Prior Publication Data
US 2022/0174805 A1    Jun. 2, 2022

Related U.S. Application Data

(63) Continuation of application No. 16/666,436, filed on Oct. 29, 2019, now Pat. No. 11,246,208.

(30) Foreign Application Priority Data

Apr. 24, 2019   (CN) .......................... 201910335861.8

(51) Int. Cl.
*H05G 1/52*   (2006.01)
*H01J 35/14*  (2006.01)
*H05G 1/58*   (2006.01)

(52) U.S. Cl.
CPC .............. *H05G 1/52* (2013.01); *H01J 35/147* (2019.05); *H05G 1/58* (2013.01)

(58) Field of Classification Search
CPC . H05G 1/52; H05G 1/56; H01J 35/153; H01J 35/066; H01J 35/147
See application file for complete search history.

(56) References Cited

U.S. PATENT DOCUMENTS

| 4,013,936 A | 3/1977 | Hesler et al. |
| 4,216,382 A | 8/1980 | Franke |

(Continued)

FOREIGN PATENT DOCUMENTS

| CN | 103491698 A | 1/2014 |
| EP | 3093867 A1 | 11/2016 |
| GB | 1357395 A | 6/1974 |

OTHER PUBLICATIONS

First Office Action in Chinese Application No. 201910335861.8 dated May 11, 2020, 12 pages.

*Primary Examiner* — Chih-Cheng Kao
(74) *Attorney, Agent, or Firm* — METIS IP LLC

(57) ABSTRACT

A method may include obtaining a feedback or a reference value of a tube voltage applied to a radiation source of a radiation device for generating radiation rays. The method may also include determining, based on the feedback or the reference value of the tube voltage, a specific value of a focusing parameter associated with a focusing device of the radiation device. The method may further include causing the focusing device to shape a focus of the radiation rays according to the determined value of the focusing parameter. The focus of the radiation rays may satisfy an operational constraint under the specific value of the focusing parameter.

20 Claims, 17 Drawing Sheets

(56) References Cited

U.S. PATENT DOCUMENTS

| | | | |
|---|---|---|---|
| 4,334,153 A | | 6/1982 | Stehman et al. |
| 4,768,216 A | * | 8/1988 | Harvey .................. H05G 1/265 |
| | | | 378/112 |
| 5,602,897 A | | 2/1997 | Kociecki et al. |
| 11,246,208 B2 | * | 2/2022 | Zhu ........................ A61B 6/405 |
| 2007/0274457 A1 | | 11/2007 | Dunham et al. |
| 2008/0130323 A1 | | 6/2008 | Wagner et al. |
| 2010/0020938 A1 | | 1/2010 | Koch et al. |
| 2012/0039443 A1 | | 2/2012 | Behling |
| 2014/0254755 A1 | | 9/2014 | Tsujino et al. |
| 2015/0098548 A1 | | 4/2015 | Bathe et al. |
| 2016/0192466 A1 | | 6/2016 | Larroux et al. |
| 2017/0086775 A1 | | 3/2017 | Madhav et al. |
| 2017/0372864 A1 | | 12/2017 | Anno et al. |
| 2019/0080876 A1 | | 3/2019 | Jeong et al. |
| 2020/0337759 A1 | | 10/2020 | Zhu et al. |
| 2020/0343069 A1 | | 10/2020 | Zhu et al. |
| 2020/0396817 A1 | | 12/2020 | Zhang et al. |
| 2021/0007210 A1 | | 1/2021 | Steadman Booker et al. |

\* cited by examiner

FIG. 2B  FIG. 2C

SYSTEMS AND METHODS FOR FOCUS CONTROL IN X-RAYS

CROSS-REFERENCE TO RELATED APPLICATIONS

This application is a continuation of U.S. patent application Ser. No. 16/666,436 filed on Oct. 29, 2019, which claims priority of Chinese Patent Application No. 201910335861.8, filed on Apr. 24, 2019, the contents of which are hereby incorporated by reference.

TECHNICAL FIELD

The disclosure generally relates to X-ray systems, and more particularly relates to systems and methods for focus control.

BACKGROUND

X-rays have been widely used in medical diagnosis, radiotherapy planning, surgery planning, radiotherapy, and other medical procedures. For example, energy imaging techniques are used to distinguish different substances of a subject based on the energy dependencies of attenuation coefficients of different substances. Using an energy imaging technique (e.g., a dual-energy imaging technique), a high voltage generator may be used to provide a tube voltage switching between a low voltage to a high voltage to a radiation source for generating radiation rays. However, the switching of the tube voltage between a high voltage and a low voltage may cause the size of a focus of the radiation rays to change, which may reduce contrast, resolution, etc., of one or more images generated using the energy imaging device. Therefore, it is desirable to provide systems and methods for shaping a focus of radiation rays in the switching of a tube voltage between a high voltage and a low voltage.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a feedback or a reference value of a tube voltage applied to a radiation source of a radiation device for generating radiation rays. The system may also determine, based on the feedback or the reference value of the tube voltage, a specific value of a focusing parameter associated with a focusing device of the radiation device. The system may further cause the focusing device to shape a focus of the radiation rays according to the determined value of the focusing parameter. The focus of the radiation rays may satisfy an operational constraint under the specific value of the focusing parameter.

In some embodiments, the system may also generate, based on at least a portion of the radiation rays detected by a detector of the radiation device, one or more images using an energy imaging technique.

In some embodiments, the operational constraint may include that a size of the focus of the radiation rays is in a range when the tube voltage changes according to a reference waveform.

In some embodiments, the operational constraint may include that a size of the focus of the radiation rays is equal to a fixed value when the tube voltage changes according to a reference waveform.

In some embodiments, the focusing device may be configured to shape the focus of the radiation rays by generating an electric field under a focusing voltage, and the focusing parameter may include the focusing voltage.

In some embodiments, the focusing device may be configured to shape the focus of the radiation rays by generating a magnetic field under a focusing current, and the focusing parameter may include the focusing current.

In some embodiments, to determine, based on the feedback or the reference value of the tube voltage, a specific value of a focusing parameter associated with a focusing device, the system may also obtain a relationship between the tube voltage and the focusing parameter with respect to a specific size of the focus; and determine, based on the relationship, the specific value of the focusing parameter corresponding to the feedback or the reference value of the tube voltage.

In some embodiments, the relationship between the tube voltage and the focusing parameter may include multiple groups of values of the tube voltage and the focusing parameter, each group may include a value of the tube voltage and a corresponding value of the focusing parameter.

In some embodiments, the relationship between the tube voltage and the focusing parameter may include multiple groups of ranges of the tube voltage and values of the focusing parameter, each group may include a range of the tube voltage and a corresponding value of the focusing parameter.

In some embodiments, to determine, based on the relationship, the specific value of the focusing parameter corresponding to the feedback or the reference value of the tube voltage, the system may determine a specific range of the tube voltage where the feedback or the reference value belongs to; and determine, based on the relationship and the specific range of the tube voltage, the specific value of the focusing parameter corresponding to the feedback or the reference value of the tube voltage.

In some embodiments, to determine, based on the feedback or the reference values of the tube voltage, a specific value of a focusing parameter associated with a focusing device, the system may obtain a relationship between the focusing parameter and time with respect to a specific size of the focus; and determine, based on the relationship and a time point when the feedback or the reference value is obtained, the specific value of the focusing parameter corresponding to the feedback or the reference value of the tube voltage.

In some embodiments, to obtain a relationship between the focusing parameter and time with respect to a specific size of the focus, the system may determine, based at least in part on a first time length that it takes for the focusing parameter to change from a minimum value to a maximum value when the tube voltage switches from a first voltage to a second voltage within the first time length, a first changing rate of the focusing parameter changing from the minimum value to the maximum value. The system may also determine, based at least in part on a second time length that it takes for the focusing parameter to change from the maximum value to the minimum value when the tube voltage switches from the second voltage to the first voltage within the second time length, a second changing rate of the focusing parameter changing from the maximum value to the minimum value. The system may further determine, based at least in part on the first changing rate or the second changing rate, the relationship between the focusing parameter and time.

According to a second aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a first reference waveform of a tube voltage of a radiation source of a radiation device, the first reference waveform may describe a change of the tube voltage with time. The system may also determine, based on the first reference waveform, a second reference waveform of a focusing parameter associated with a focusing device of the radiation device, the second reference waveform may describe a change of the focusing parameter with time. The system may further cause a high voltage generator to provide the tube voltage according to the first reference waveform to the radiation source for generating radiation rays; and cause the focusing device to shape a focus of the radiation rays according to the second reference wave, wherein the focus of the radiation rays satisfies an operational constraint when the tube voltage changes according to the first reference waveform.

In some embodiments, the first reference waveform may be defined by one or more switching parameters of the tube voltage, and the one or more switching parameters may include at least one of a first voltage, a second voltage higher than the first voltage, a first time length that it takes for the tube voltage to change from the first voltage to the second voltage, a second time length that it takes for the tube voltage to change from the second voltage to the first voltage, a third time length that the tube voltage is maintained at the first voltage, or a fourth time length that the tube is maintained at the second voltage.

In some embodiments, to determine, based on the first reference waveform, a second reference waveform of a focusing parameter associated with a focusing device, the system may determine, based at least in part on the first time length, a first changing rate of the focusing parameter changing from a minimum value to a maximum value of the focusing parameter when the tube voltage switches from the first voltage to the second voltage within the first time length. The system may also determine a second changing rate of the focusing parameter when the tube voltage changes from the maximum value to the minimum value within the second time length. The system may further determine, based at least in part on the first changing rate and the second changing rate, the second reference waveform.

In some embodiments, to determine, based at least in part on the first time length, a first changing rate and determine, based at least in part on the second time length, a second changing rate, the system may determine, based on the first voltage, the minimum value of the focusing parameter and determine, based on the second voltage, the maximum value of the focusing parameter. The system may also determine, based on the first time length, the maximum value, and the minimum value, the first changing rate of the focusing parameter and determine, based on the second time length, the maximum value, and the minimum value, the second changing rate of the focusing parameter.

In some embodiments, to determine, based on the first reference waveform, a second reference waveform of a focusing parameter associated with a focusing device, the system may determine multiple values of the tube voltage during the first time length. The system may also determine, based on the multiple values of the tube voltage during the first time length, multiple values of the focusing parameter each of which corresponds to one of the multiple values of the tube voltage. The system may further determine, based at least in part on the multiple values of the focusing parameter during the first time length, the second reference waveform.

In some embodiments, to determine, based on the multiple values of the tube voltage during the first time length, multiple values of the focusing parameter each of which corresponds to one of the multiple values of the tube voltage, the system may obtain a relationship between the tube voltage and the focusing parameter with respect to a specific size of the focus; and determine, based on the relationship and the multiple values of the tube voltage, the multiple values of the focusing parameter.

In some embodiments, the system may further obtain projection data generated by detecting at least a portion of the radiation rays by a detector of the radiation device, and generate, based on the projection data, one or more images using an energy imaging technique.

According to a third aspect of the present disclosure, a method is provided. The method may be implemented on at least one computing device, each of which may include at least one processor and a storage device. The method may include obtaining in real time a feedback or a reference value of a tube voltage applied to a radiation source of a radiation device for generating radiation rays. The method may also include determining, based on the feedback or the reference value of the tube voltage, a specific value of a focusing parameter associated with a focusing device of the radiation device. The method may further include causing the focusing device to shape a focus of the radiation rays according to the determined value of the focusing parameter. The focus of the radiation rays may satisfy an operational constraint under the specific value of the focusing parameter.

According to a fourth aspect of the present disclosure, a method is provided. The method may be implemented on at least one computing device, each of which may include at least one processor and a storage device. The method may include obtaining a first reference waveform of a tube voltage of a radiation source of a radiation device, the first reference waveform describing a change of the tube voltage with time. The method may also include determining, based on the first reference waveform, a second reference waveform of a focusing parameter associated with a focusing device of the radiation device, the second reference waveform describing a change of the focusing parameter with time. The method may further include causing a high voltage generator to provide the tube voltage according to the first reference waveform to the radiation source for generating radiation rays; and causing the focusing device to shape a focus of the radiation rays according to the second reference wave, wherein the focus of the radiation rays satisfies an operational constraint when the tube voltage changes according to the first reference waveform.

According to a fifth aspect of the present disclosure, a non-transitory computer readable medium is provided. The non-transitory computer readable medium may include a set of instructions. When executed by at least one processor, the set of instructions may direct the at least one processor to effectuate a method. The method may include obtaining in real time a feedback or a reference value of a tube voltage applied to a radiation source of a radiation device for generating radiation rays. The method may also include determining, based on the feedback or the reference value of the tube voltage, a specific value of a focusing parameter associated with a focusing device of the radiation device. The method may further include causing the focusing device to shape a focus of the radiation rays according to the determined value of the focusing parameter. The focus of the radiation rays may satisfy an operational constraint under the specific value of the focusing parameter.

According to a sixth aspect of the present disclosure, a non-transitory computer readable medium is provided. The non-transitory computer readable medium may include a set of instructions. When executed by at least one processor, the set of instructions may direct the at least one processor to effectuate a method. The method may include obtaining a first reference waveform of a tube voltage of a radiation source of a radiation device, the first reference waveform describing a change of the tube voltage with time. The method may also include determining, based on the first reference waveform, a second reference waveform of a focusing parameter associated with a focusing device of the radiation device, the second reference waveform describing a change of the focusing parameter with time. The method may further include causing a high voltage generator to provide the tube voltage according to the first reference waveform to the radiation source for generating radiation rays; and causing the focusing device to shape a focus of the radiation rays according to the second reference waveform, wherein the focus of the radiation rays satisfies an operational constraint when the tube voltage changes according to the first reference waveform.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 2B is a schematic diagram illustrating an exemplary focusing device according to some embodiments of the present disclosure;

FIG. 2C is a schematic diagram illustrating an exemplary focusing device according to some embodiments of the present disclosure;

DETAILED DESCRIPTION

Figure 1:
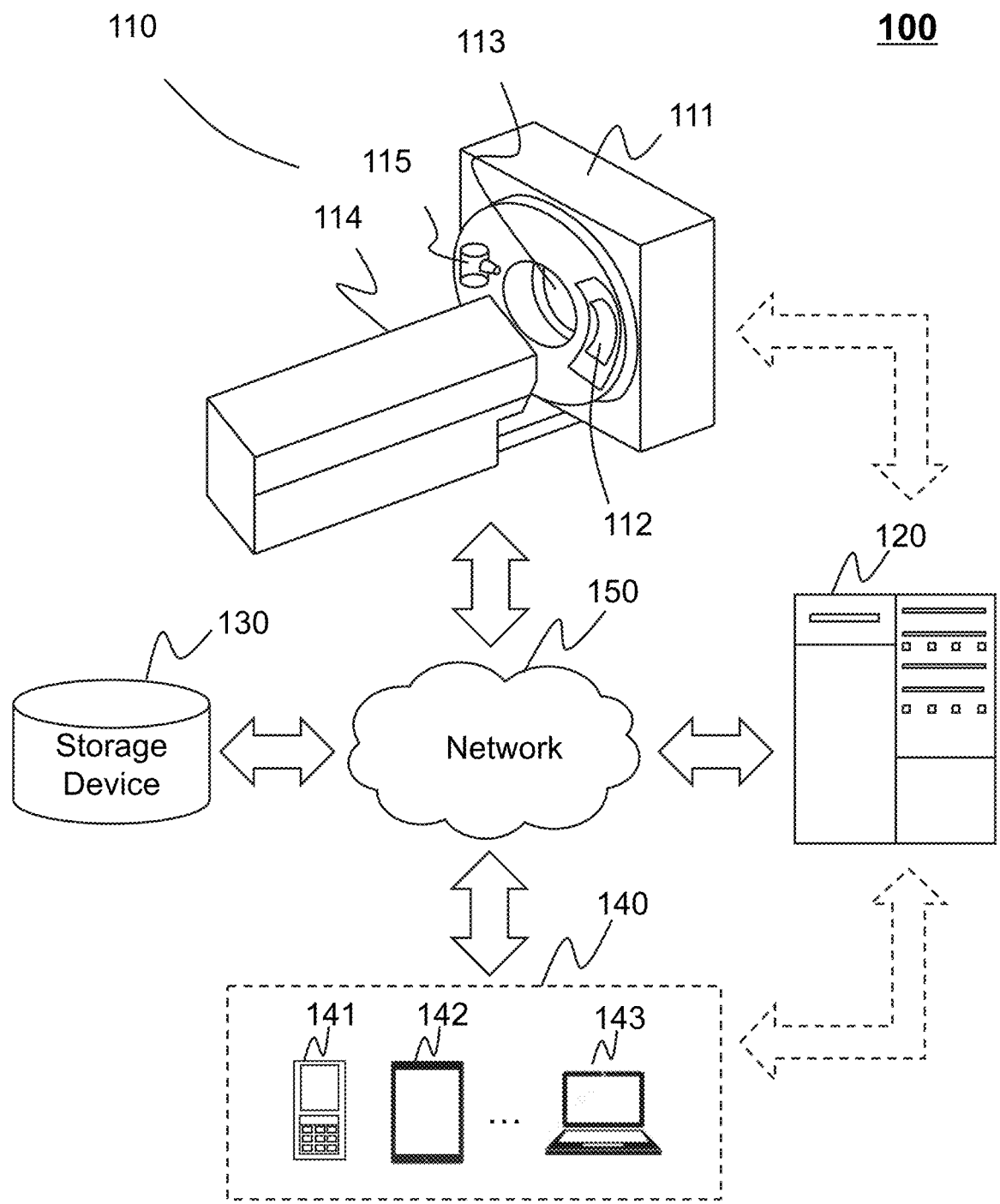
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for focus control of x-rays. The system may include at least one storage device storing executable instructions, and at least one processor in communication with the at least one storage device. When executing the executable instructions, the at least one processor may cause the system to obtain in real time a feedback of a tube voltage applied to a radiation source of a radiation device for generating radiation rays. The at least one processor may also cause the system to determine, based on the feedback of the tube voltage, a specific value of a focusing parameter associated with a focusing device of the radiation device. The at least one processor may further cause the system to cause the focusing device to shape a focus of the radiation rays according to the determined value of the focusing parameter. The focus of the radiation rays may satisfy an operational constraint under the specific value of the focusing parameter. The radiation device may include an imaging device, a treatment device, etc. In some embodiments, if the radiation device is an imaging device including a detector, the at least one processor may further cause the system to obtain projection data generated by detecting at least a portion of the radiation rays by the detector.

Accordingly, the system may adjust the focusing parameter associated with the focusing device in real time according to feedbacks of the tube voltage of the radiation source so that the size of the focus of radiation rays may satisfy an operational constraint during the switching of the tube voltage. The operational constraint may include that the size of the focus of radiation rays is equal to a fixed value or in a range. Therefore, the size of the focus of radiation rays during an imaging scan may be considered to constant, thereby improving quality (e.g. contrast, resolution, etc.) of one or more images generated using an energy imaging technique (e.g., a dual-energy imaging technique).

It should be noted that the imaging system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure. For example, the systems and methods for focus control may be used in a treatment system, such as an image-guided radiotherapy (IGRT) system, an X-ray treatment system, etc. Merely by way of example, the IGRT system may include, for example, a CT guided radiotherapy system.

FIG. 1 is a schematic diagram illustrating an exemplary imaging system according to some embodiments of the present disclosure. In some embodiments, the imaging system 100 may be applied to any application scenario in which radiation rays (e.g., X-rays) are used for generating images and/or providing treatment, such as a computed tomography (CT) system, a digital radiography (DR) system, a C-arm X-ray system, a computed tomography-positron emission tomography (CT-PET) system, an image-guide radiotherapy (IGRT) system (e.g., a CT guided radiotherapy system), or the like, or a combination thereof.

As illustrated in FIG. 1, the imaging system 100 may include an imaging device 110, a processing device 120, a storage device 130, one or more terminals 140, and a network 150. The components in the imaging system 100 may be connected in one or more of various ways. Merely by way of example, the imaging device 110 may be connected to the processing device 120 through the network 150. As another example, the imaging device 110 may be connected to the processing device 120 directly as indicated by the bi-directional arrow in dotted lines linking the imaging device 110 and the processing device 120. As a further example, the storage device 130 may be connected to the processing device 120 directly or through the network 150. As still a further example, the terminal 140 may be connected to the processing device 120 directly (as indicated by the bi-directional arrow in dotted lines linking the terminal 140 and the processing device 120) or through the network 150.

The imaging device 110 may be configured to scan a subject using radiation rays and generate imaging data used to generate one or more images relating to the subject. The imaging data relating to at least one part of the subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. In some embodiments, the imaging device 110 may transmit the imaging data to the processing device 120 for further processing (e.g., generating one or more images). In some embodiments, the imaging data and/or the one or more images associated with the subject may be stored in the storage device 130 and/or the processing device 120. In some embodiments, the imaging device 110 may include a computed tomography (CT) scanner, a digital radiography (DR) scanner, a C-arm X-ray scanner, a digital subtraction angiography (DSA) scanner, a dynamic spatial reconstructor (DSR) scanner, an X-ray microscopy scanner, a multi-modality scanner, or the like, or a combination thereof. Exemplary multi-modality scanners may include a computed tomography-positron emission tomography (CT-PET) scanner, a computed tomography-magnetic resonance imaging (CT-MRI) scanner, etc. In some embodiments, one or more components in the imaging system 100 may be omitted. Merely by way of example, the imaging system 100 may not include the terminal(s) 140.

The imaging device 110 may include a gantry 111, one or more detectors, a detecting region 113, a table 114, a radiation source 115, or any other component. The gantry 111 may be configured to provide support for other components (e.g., the radiation source 115, the detector(s) 112, etc.) of the imaging device 110. In some embodiments, the detector(s) 112 and the radiation source 115 may be oppositely mounted on the gantry 111. In some embodiments, the gantry 111 may rotate and/or move. The detector(s) 112 and the radiation source 115 may rotate along with the rotation of the gantry 111. The table 114 may be configured to locate and/or support a scanned object. A scanned object may be placed on the table 114 and moved into the detecting region 113 (e.g., a space between the detector(s) 112 and the radiation source 115) of the imaging device 110. The scanned object may be biological or non-biological. Merely by way of example, the scanned object may include a patient, a man-made object, etc. As another example, the scanned object may include a specific portion, organ, and/or tissue of the patient. For example, the scanned object may include head, brain, neck, body, shoulder, arm, thorax, heart, stomach, blood vessel, soft tissue, knee, feet, or the like, or any combination thereof. In the present disclosure, "subject", "object" or "scanned object" are used interchangeably.

The radiation source 115 may be configured to generate and/or emit radiation rays (e.g., X-rays) to scan the scanned object that is placed on the table 114. In some embodiments, the radiation source 115 may include a high voltage generator, one or more tubes, or any other components (e.g., a collimator). The high voltage generator may be configured to provide a voltage and/or current for the tube, and/or provide power for other components (e.g., a cathode filament) of the radiation source 115. The high voltage generator may include a controller, an inverter circuit, a high voltage generating circuit, a rectifier, or any other modules (e.g., a driving circuit). More descriptions regarding the high voltage generator may be found in, e.g., U.S. application Ser. No. 16/666,438, entitled "SYSTEMS AND METHODS FOR HIGH VOLTAGE GENERATION," filed on even date, which is incorporated by reference. The tube may be configured to generate radiation rays when a voltage is applied to the tube by the high voltage generator. As used herein, the voltage applied to the tube may be also referred to as a tube voltage. In some embodiments, the tube may include a cathode filament and an anode target. The voltage generated by the high-voltage generator may trigger the cathode filament to emit a plurality of electrons to form an electron beam. The emitted electron beam may be impinged on a small area (i.e., the focus) on the anode target to generate radiation beams (e.g., X-rays beams) consisting of high-energetic photons. In some embodiments, the radiation rays may include X-rays, γ-rays, α-rays, or the like, or a combination thereof. In some embodiments, the radiation source 115 may further include a focusing device configured to shape a focus of radiation rays generated by the tube. In some embodiments, more descriptions for the radiation source 115 may be found elsewhere in the present disclosure (e.g., FIG. 2A and the descriptions thereof). The detector(s) 112 may detect the radiation beams penetrated through at least part of the scanned object within the detection region 113. In some embodiments, the imaging device 110 may include one single detector which may be configured to detect at least a portion of the radiation rays emitted by the radiation source 115 when the tube voltage of the tube switches between a first voltage and a second voltage higher than the first voltage. In some embodiments, the imaging device 110 may include two detectors. One detector may be configured to detect a first portion of the radiation rays emitted by the radiation source 115 responding to a first voltage, and another detector may be configured to detect a second portion of the radiation rays emitted by the radiation source 115 responding to a second voltage higher than the first voltage. In some embodiments, the detector(s) 112 may include a plurality of detector units, which may be arranged in any suitable manner, for example, a channel direction and a row direction. The detector(s) 112 may include a scintillation detector (e.g., a cesium iodide detector), a gas detector, etc.

The processing device 120 may process data and/or information obtained from the imaging device 110, the terminal(s) 140, and/or the storage device 130. For example, the processing device 120 may obtain a first reference waveform of a tube voltage of a radiation source of a radiation device. The radiation device may include an imaging device (e.g., the imaging device 110), a treatment device (e.g., an X-ray treatment machine, etc. The first reference waveform may describe a change of the tube voltage along with time. The processing device 120 may determine, based on the first reference waveform, a second reference waveform of a focusing parameter associated with a focusing device, the second reference waveform describing a change of the focusing parameter with time. The processing device 120 may cause a high voltage generator to provide the tube voltage according to the first reference waveform to the radiation source for generating radiation rays. The processing device 120 may cause the focusing device to shape a focus of the radiation rays according to the second reference waveform, wherein the focus of the radiation rays satisfies an operational constraint when the tube voltage changes according to the first reference waveform. The processing device 120 may obtain projection data generated by detecting at least a portion of the radiation rays by a detector of the radiation device. The processing device 120 may be a central processing unit (CPU), a digital signal processor (DSP), a system on a chip (SoC), a microcontroller unit (MCU), or the like, or any combination thereof.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the imaging device 110, the terminal(s) 140, and/or the storage device 130 via the network 150. As another example, the processing device 120 may be directly connected to the imaging device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented on a computing device 300 having one or more components illustrated in FIG. 2 in the present disclosure.

The storage device 130 may store data, instructions, and/or any other information. In some embodiments, the storage device 130 may store data obtained from the terminal(s) 140 and/or the processing device 120. For example, the storage device 130 may store one or more images obtained from the processing device 120. In some embodiments, the storage device 130 may store data and/or instructions that the processing device 120 may execute or use to perform exemplary methods/systems described in the present disclosure. For example, the storage device 130 may store data and/or instructions that the processing device 120 may execute or use to generate an image that satisfies target brightness. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components of the imaging system 100 (e.g., the processing device 120, the terminal(s) 140, etc.). One or more components of the imaging system 100 may access the data or instructions stored in the storage device 130 via the network 150. In some embodiments, the storage device 130 may be directly connected to or communicate with one or more other components of the imaging system 100 (e.g., the processing device 120, the terminal(s) 140, etc.). In some embodiments, the storage device 130 may be part of the processing device 120.

The terminal(s) 140 may include a mobile device 141, a tablet computer 142, a laptop computer 143, or the like, or any combination thereof. In some embodiments, the mobile device 141 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may remotely operate the imaging device 110. In some embodiments, the terminal(s) 140 may operate the imaging device 110 via a wireless connection. In some embodiments, the terminal(s) 140 may receive information and/or instructions inputted by a user, and send the received information and/or instructions to the imaging device 110 or to the processing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

The network 150 may include any suitable network that can facilitate the exchange of information and/or data for the imaging system 100. In some embodiments, one or more components of the imaging system 100 (e.g., the imaging device 110, the terminal(s) 140, the processing device 120, the storage device 130) may communicate information and/or data with one or more other components of the imaging system 100 via the network 150. For example, the processing device 120 may obtain data from the imaging device 110 via the network 150. As another example, the processing device 120 may obtain user instructions from the terminal(s) 140 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. For instance, the system 100 may be a system including a radiation device 110. The system 100 may be configured to deliver radiation for imaging and/or treatment purposes. The disclosure with reference to the device 110 being an imaging device for illustration purposes and not intended to be limiting.

Figure 2A:
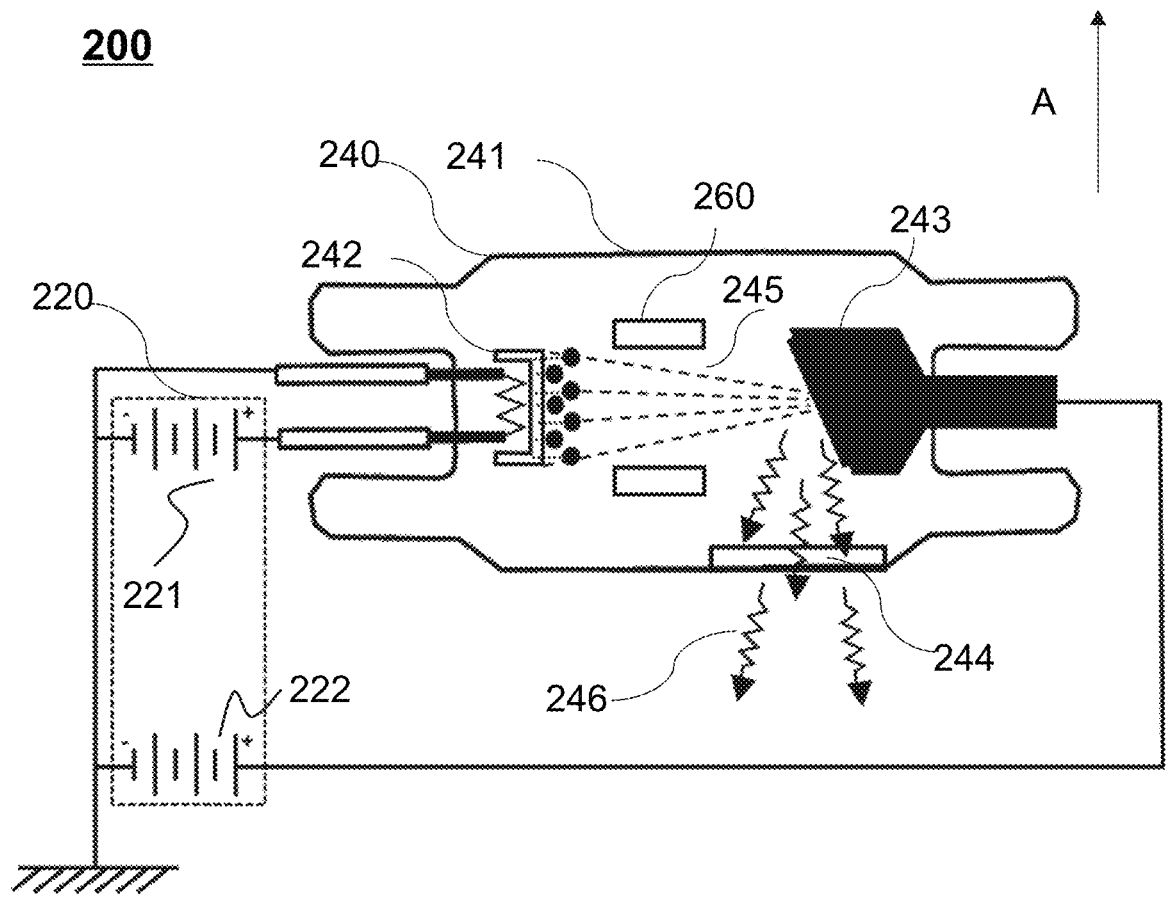
FIG. 2A is a schematic diagram illustrating an exemplary radiation source according to some embodiments of the present disclosure.
Figure 2D:
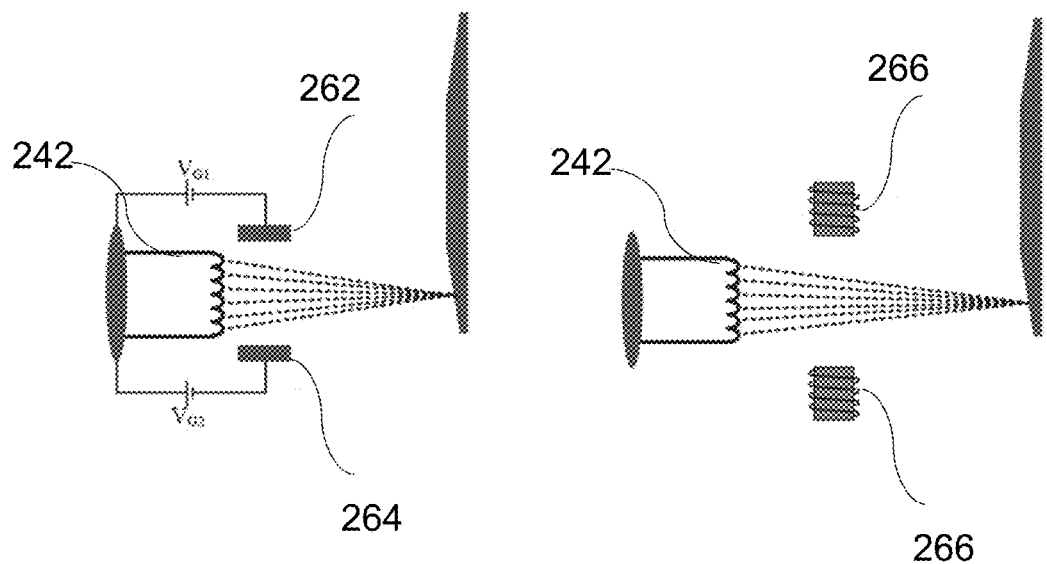
FIG. 2D is a schematic diagram illustrating exemplary changing curves of a tube voltage and a focusing parameter according to some embodiments of the present disclosure.
Figure 2D:
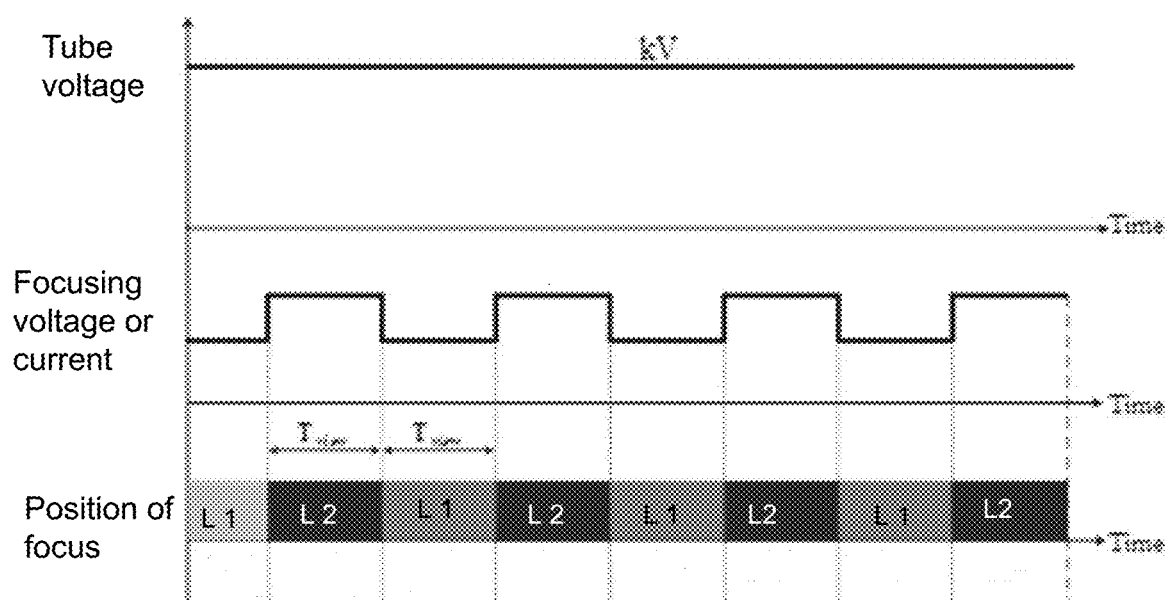

FIG. 2A is a schematic diagram illustrating an exemplary radiation source according to some embodiments of the present disclosure. As shown in FIG. 2, the radiation source 200 may include a high voltage generator 220, a tube 240, and a focusing device 260. The high voltage generator 220 may be configured to provide a tube voltage and/or tube current for the tube 240, and/or provide power for other components of the tube 240. For example, the high voltage generator 220 may include a high voltage generating module 222 configured to provide a tube voltage between a cathode and an anode of the tube 240. As another example, the high voltage generator 220 may include a filament power supply 221 configured to provide a current for a cathode filament 242 of the tube 240.

In some embodiments, the tube 240 may include a cold cathode ion tube, a high vacuum hot cathode tube, a rotating anode tube, etc. As illustrated in FIG. 2, the tube 240 may include a shell 241, a cathode filament 242, an anode target 243, and a window 244. The shell 241 may be configured to support at least one of the cathode filament 242, the anode target 243, or any other components of the tube 240, and provide a certain condition for radiation beams generated by the cathode filament 242, for example, a certain vacuum degree. In some embodiments, the shell 241 may be made of glass and/or ceramic.

The cathode filament 242 may be configured to emit electrons. In some embodiments, the anode target 243 may have a tilt angle which may be defined as an angle of the surface of the anode target 243 with respect to a direction (denoted by arrow A as shown in FIG. 2A) perpendicular to an axial direction of the tube 240 of radiation rays 246. The cathode filament 242 may be the cathode of the tube 240 and the anode target 243 may be the anode of the tube 240.

A high voltage (i.e., tube voltage) may be provided between the cathode filament 242 and the anode target 243 by the high voltage generator 220 (e.g., the high voltage generating module 222). An electric field may be formed based on the tube voltage to cause electrons emitted from the cathode filament 242 to form an electron beam 245. The electric field may accelerate the electron beam 245 to impinge an area on the anode target 243. Then radiation rays 246 may be generated by the anode target 243. The window 244 may allow the radiation rays 246 to pass through and emitted to radiate a subject.

The focusing device 260 may be configured to shape a focus of the radiation rays 246 generated by the anode target 243. For example, the focusing device 260 may adjust a size of the focus of the radiation rays 246 in a range when the tube voltage provided by the high voltage generator 220 changes by adjusting the focusing parameter. As another example, the focusing device 260 may keep or maintain the size of the focus of the radiation rays 246 to be equal to a fixed value when the tube voltage provided by the high voltage generator 220 changes by adjusting the focusing parameter. In some embodiments, a focus may be also referred to as a focal point or focal spot. The focus of the radiation rays 246 may be an actual focus and/or an effective focus. As used herein, the actual focus of the radiation rays may refer to an area of electrons of the electron beam 245 impinging on a surface of the anode target 243. The actual focus of the radiation rays may be also referred to as a size of the electrons of the electron beam 245. The effective focus of the radiation rays 246 may refer to a projection of the actual focus along a direction (denoted by arrow A in FIG. 2A) perpendicular to the axial direction of the tube 240.

Different configurations of the focusing devices may correspond to different focusing parameters. For example, the focusing device 260 may be configured to shape the focus of the radiation rays 246 by generating an electric field when a focusing voltage is applied to the focusing device 260 by a power. The electric field generated by the focusing device 260 may be also referred to as a focusing electric field. The focusing parameter may include the focusing voltage. As another example, the focusing device 260 may be configured to shape the focus of the radiation rays 246 by generating a magnetic field when a focusing current is applied to the focusing device 260 by a power. The magnetic field generated by the focusing device 260 may be also referred to as a focusing magnetic field. The focusing parameter may include the focusing current, also referred to as coil current. More descriptions for the focusing device 260 may be found in FIGS. 2B and 2C.

It should be noted that the above description of the radiation source 115 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the assembly and/or function of the radiation source 115 may be varied or changed according to specific implementation scenarios. For example, the radiation source 200 may also include a deflector which may be provided between the focusing device 260 and the anode target 243. The deflector may be configured to deflect or change the path of electrons emitted from the cathode filament 242. The position of the focus (e.g., the actual focus and/or the effective focus) may be changed by deflecting or changing the path of the electrons.

FIG. 2B is a schematic diagram illustrating an exemplary focusing device 260 according to some embodiments of the present disclosure. As shown in FIG. 2B, the focusing device 260 may include two grid plates 262 and 264. A focusing electric field may be generated between the two grid plates 262 and 264 when a focusing voltage is applied between the two grid plates. In some embodiments, the focusing device 260 may further include a power configured to provide the focusing voltage between the two grid plates 262 and 264. The electron beam generated by the cathode filament 242 may pass through a space between the two grid plates 262 and 264 and shaped by the focusing electric field. The focusing electric field may be changed with the change of the focusing voltage.

FIG. 2C is a schematic diagram illustrating an exemplary focusing device 260 according to some embodiments of the present disclosure. As shown in FIG. 2C, the focusing device 260 may include an electromagnet 266. The electromagnet 266 may include a coil and a magnet. A focusing magnet field may be generated when a focusing current is provided to the electromagnet 266. The electron beam generated by the cathode filament 242 may pass through a space in the electromagnet 266 and shaped by the focusing magnet field. In some embodiments, the focusing device 260 may further include a power configured to provide the focusing current to the electromagnet 266. The focusing magnetic field may be changed with the change of the focusing current.

In some embodiments, the focusing device 260 may adjust values of the focusing voltage or current according to the change of the tube voltage to focusing the size of the focus equal to a fixed value or in a range. In some embodiments, the focusing device 260 may adjust a position of the focus of the radiation rays by adjusting values of the focusing voltage so as to increase the sampling rate of the projection, thus improve the image quality. FIG. 2D is a schematic diagram illustrating exemplary changing curves of a tube voltage and a focusing parameter according to some embodiments of the present disclosure. As shown in FIG. 2D, when the tube voltage is unchanged or constant, the focusing device 260 may adjust the focusing voltage or current to changing the position of the focus switching between position L1 and position L2. The switching of the position of the focus may improve a spatial resolution of one or more images generated based on radiation rays detected by a detector.

Figure 3:
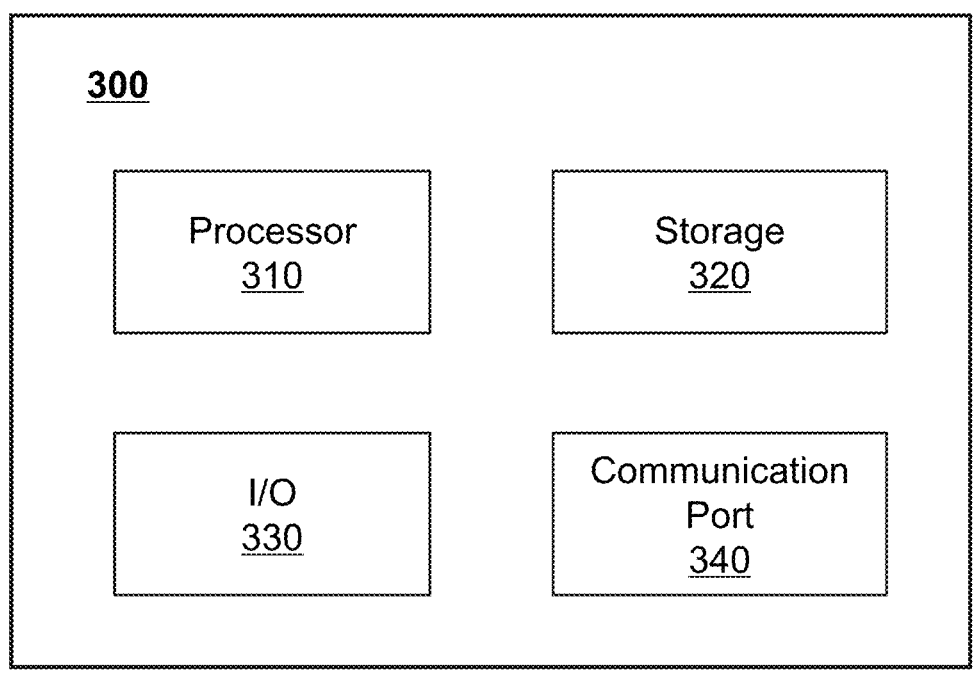
FIG. 3 is a schematic diagram illustrating hardware and/or software components of an exemplary computing device according to some embodiments of the present disclosure.

FIG. 3 is a schematic diagram illustrating hardware and/or software components of an exemplary computing device 300 on which the processing device 120 may be implemented according to some embodiments of the present disclosure. As illustrated in FIG. 2, the computing device 300 may include a processor 310, a storage 320, an input/output (I/O) 330, and a communication port 340.

The processor 310 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 310 may process data obtained from the imaging device 110, the terminal(s) 140, the storage device 130, and/or any other component of the imaging system 100. Specifically, the processor 310 may process one or more measured data sets obtained from the imaging device 110. For example, the processor 310 may reconstruct an image based on the data set(s). In some embodiments, the reconstructed image may be stored in the storage device 130, the storage 320, etc. In some embodiments, the reconstructed image may be displayed on a display device by the I/O 330. In some embodiments, the processor 310 may perform instructions obtained from the terminal(s) 140. In some embodiments, the processor 310 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the imaging device 110, the terminal(s) 140, the storage device 130, or any other component of the imaging system 100. In some embodiments, the storage 320 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for generating attenuation correction data for a PET image.

The I/O 330 may input or output signals, data, and/or information. In some embodiments, the I/O 330 may enable user interaction with the processing device 120. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected with a network (e.g., the network 150) to facilitate data communications. The communication port 340 may establish connections between the processing device 120 and the imaging device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
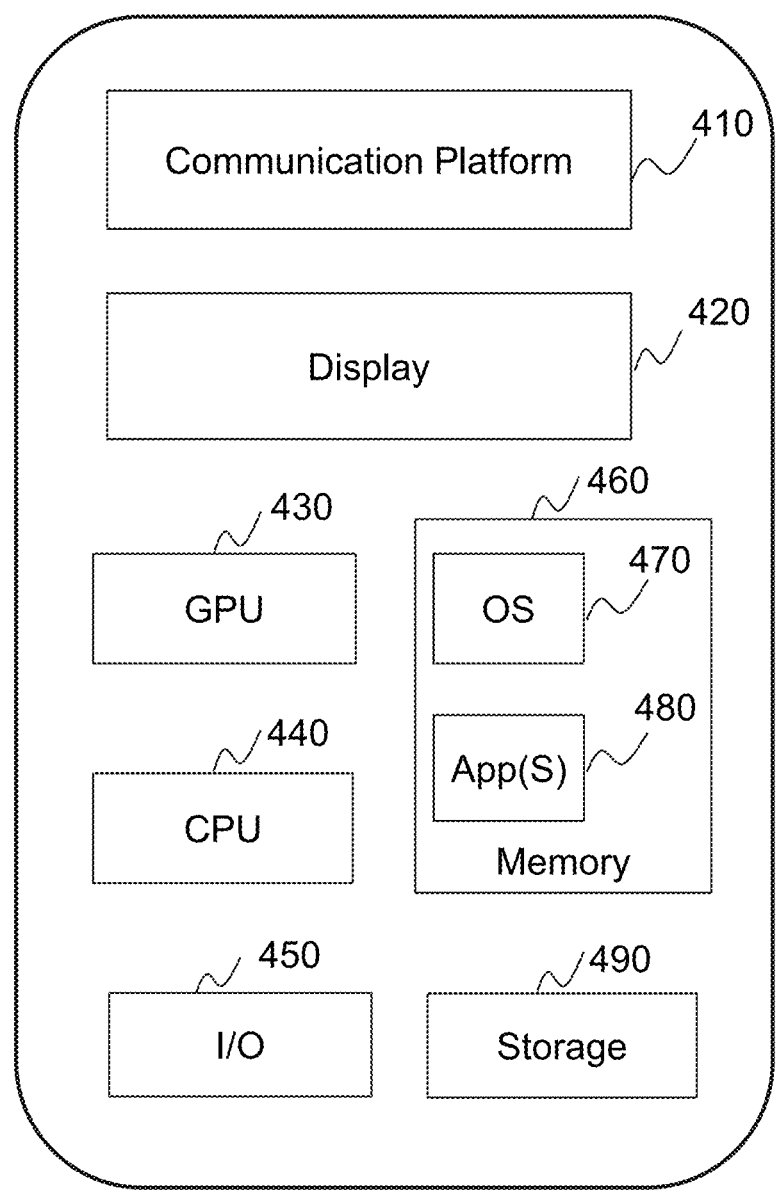
FIG. 4 is a schematic diagram illustrating hardware and/or software components of an exemplary mobile device according to some embodiments of the present disclosure.

FIG. 4 is a schematic diagram illustrating hardware and/or software components of an exemplary mobile device 400 according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 5:
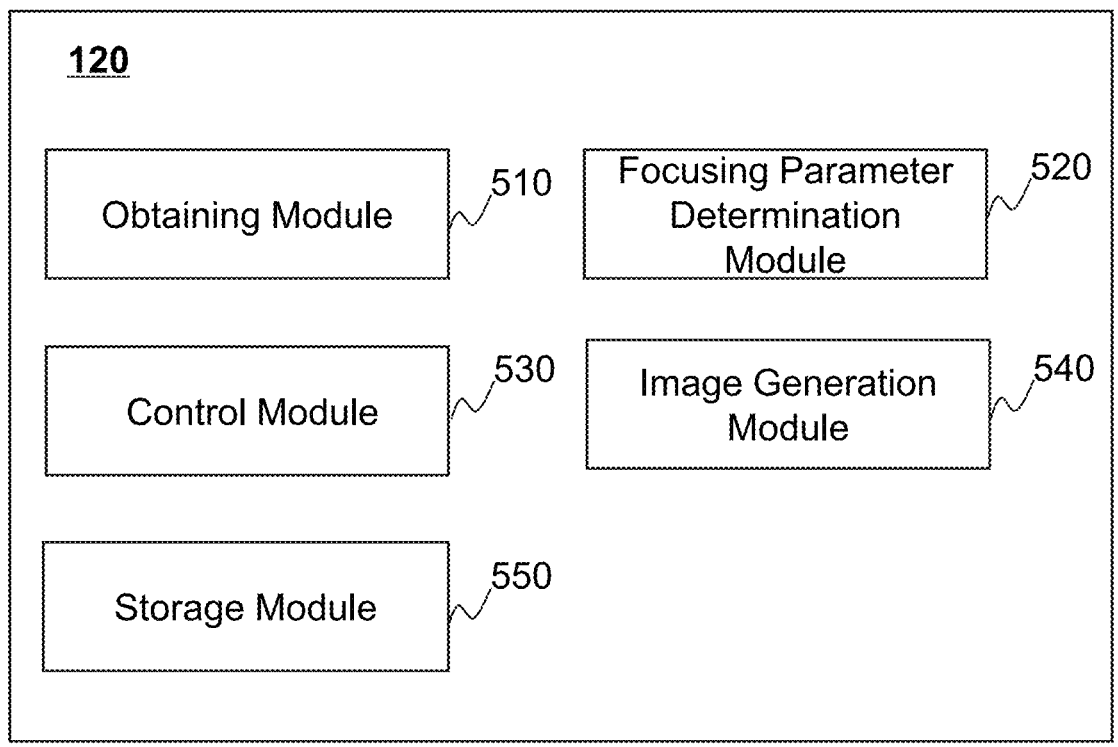
FIG. 5 is a block diagram illustrating exemplary processing device according to some embodiments of the present disclosure.

FIG. 5 is a block diagram illustrating exemplary processing device 120 according to some embodiments of the present disclosure. In some embodiments, the processing device 120 may be implemented on a computing device 300 (e.g., the processor 310) illustrated in FIG. 3 or a CPU 440 as illustrated in FIG. 4. As illustrated in FIG. 5, the processing device 120 may include an obtaining module 510, a focusing parameter determination module 520, a control module 530, an image generation module 540, and a storage module 550. Each of the modules described above may be a hardware circuit that is designed to perform certain actions, e.g., according to a set of instructions stored in one or more storage media, and/or any combination of the hardware circuit and the one or more storage media.

The obtaining module 510 may be configured to obtain a first reference waveform of a tube voltage of a radiation source of a radiation device. In some embodiments, the radiation source (e.g., an imaging device) may include a tube, a high voltage generator, etc. The high voltage generator may be configured to provide the tube voltage for the tube. The tube may emit radiation rays (also referred to as radiation beams) based on the tube voltage.

In some embodiments, the obtaining module 510 may obtain the first reference waveform from the imaging device 110, the storage device 130, the terminal(s) 140, or any other storage device. In some embodiments, the obtaining module 510 may obtain the first reference waveform from a database (e.g., the storage device 130) storing multiple first reference waveforms. Each of the multiple first reference waveforms may correspond to a scanning protocol. The obtaining module 510 may retrieve the first reference waveform from the database based on a specific scanning protocol.

In some embodiments, the obtaining module 510 may be further configured to obtain in real time a feedback of the tube voltage. The feedback of the tube voltage may refer to an actual value of the tube voltage that the high voltage generator generates and provides to the tube in a procedure using the radiation rays. In some embodiments, the feedback of the tube voltage may be acquired and/or collected by a controller of the high voltage generator. The obtaining module 510 may obtain the feedback of the tube voltage from the controller of the high voltage generator. In some embodiments, the feedback of the tube voltage may be acquired and/or collected in real time by a voltage sensor. The obtaining module 510 may obtain the feedback of the tube voltage from the voltage sensor.

In some embodiments, the first reference waveform may include a plurality of first points. Each of the plurality of first points may be defined by a time point and a value of the tube voltage corresponding to the time point. In some embodiments, the first reference waveform may include a plurality of first sections corresponding to different time periods according to the change of the tube voltage. For example, the first reference waveform may include a rising edge describing that the tube voltage increases from a first voltage to a second voltage higher than the first voltage, a falling edge describing that the tube voltage decreases from the second voltage to the first voltage, a platform stage of a low voltage describing that the tube voltage is maintained at the first voltage, and a platform stage of a high voltage describing that the tube voltage is maintained at the second voltage. In some embodiments, the first reference waveform may be defined by one or more switching parameters of the tube voltage. The one or more switching parameters may include a first voltage, a second voltage higher than the first voltage, a first time length (i.e., a transition time of a rising edge) that it takes for tube voltage to change from the first voltage to the second voltage, a second time length (i.e., a transition of a falling edge) that it takes for the tube voltage changes from the second voltage to the first voltage, a third time length that the tube voltage is maintained at the first voltage, a fourth time length that the tube is maintained at the second voltage, switching time points, or the like, or any combination thereof.

The focusing parameter determination module 520 may be configured to determine a second reference waveform of a focusing parameter associated with a focusing device based on the first reference waveform. The focusing device may be configured to shape a focus of radiation rays generated by the radiation source.

In some embodiments, the second reference waveform may include a plurality of second points. Each of the plurality of second points may be defined by a time point and a value of the focusing parameter (e.g., a focusing voltage, a focusing current). Each of the plurality of second points of the second reference waveform may correspond to one of the plurality of first points of the first reference waveform. The focusing parameter determination module 520 may determine each of the plurality of second points based on the corresponding first point. For example, the focusing parameter determination module 520 may obtain a relationship between the tube voltage and the focusing parameter with respect to a specific size of the focus. The specific size of the focus may be equal to or close to a desired specific size of the focus. The relationship between the tube voltage and the focusing parameter may provide multiple groups of values or ranges of the tube voltage and values of the focusing parameter. Each group of the multiple groups may include a value or a range of the tube voltage and a corresponding value of the focusing parameter. The focusing parameter determination module 520 may determine a value of the focusing parameter corresponding to a specific second point based on the relationship and a value of the tube voltage corresponding to the specific first point.

In some embodiments, the second reference waveform may include a plurality of second sections corresponding to different time periods. Each of the plurality of second sections may correspond to one of the plurality of the first sections of the first reference waveform. The focusing parameter determination module 520 may determine the second reference waveform based on the switching parameters of the first reference waveform. Further, the focusing parameter determination module 520 may determine each of the plurality of second sections based on the one or more switching parameters of the tube voltage associated with the corresponding first section. For example, the focusing parameter determination module 520 may determine a minimum value of the focusing parameter based on the first voltage and determine a maximum value of the focusing parameter based on the second voltage according to the relationship between the focusing parameter and the tube voltage with respect to a specific size of the focus. The focusing parameter determination module 520 may determine a low-parameter platform stage of the second reference waveform based on the minimum value of the focusing parameter and the third time length that the tube voltage is maintained at the first voltage. The focusing parameter determination module 520 may determine a high-parameter platform stage of the second reference waveform based on the maximum value of the focusing parameter and the fourth time length that the tube voltage is maintained at the second voltage. The focusing parameter determination module 520 may determine a first changing rate of the focusing parameter changing from the minimum value to the maximum value based on the first time length it takes for the tube voltage to change from the first voltage to the second voltage. The focusing parameter determination module 520 may determine a rising edge of the second reference waveform based on the first changing rate and the first time length it takes for the tube voltage changes from the first voltage to the second voltage. The focusing parameter determination module 520 may determine a second changing rate of the focusing parameter changing from the maximum value to the minimum value based on the second time of duration. The focusing parameter determination module 520 may determine a falling edge of the second reference waveform based on the second changing rate and the second time length it takes for the tube voltage changes from the second voltage to the first voltage. The first changing rate and the second changing rate may be also referred to as a slope of the rising edge and the falling edge of the second reference waveform, respectively. The focusing parameter determination module 520 may determine the second reference waveform based on the determined falling edge, the determined rising edge, the determined low-parameter platform stage, and the determined high-parameter platform stage. In some embodiments, the focusing parameter determination module 520 may determine a rising edge and/or a falling edge of the second reference waveform by determining multiple changing rates of the focusing parameter in the first time length and/or the second time length.

In some embodiments, the focusing parameter determination module 520 may be further configured to determine a specific value of a focusing parameter associated with the focusing device based on the feedback of the tube voltage. In some embodiments, the focusing parameter determination module 520 may obtain a relationship between the tube voltage and the focusing parameter with respect to a specific size of a focus or a specific range of the size of the focus. The focusing parameter determination module 520 may determine the specific value of the focusing parameter based on the feedback of the tube voltage and the relationship.

The control module 530 may be configured to cause the high voltage generator to provide the tube voltage according to the first reference waveform to the radiation source for generating radiation rays. The control module 530 may be further configured to cause the focusing device to shape a focus of the radiation rays according to the second reference waveform. The control module 530 may receive the reference waveform (e.g., the first reference waveform, the second reference waveform) in the form of instructions. The control module 530 may cause the high voltage generator to generate the tube voltage according to the first reference waveform in response to the receipt of a first exposure instruction from the processing device 120 or the terminal 140. The control module 530 may control a power to provide the focusing parameter (e.g., a focusing voltage, a focusing current) with specific values according to the second reference waveform in response to the receipt of a second exposure instruction from the processing device 120 or the terminal 140. The focusing parameter with a specific value at a specific time point may be provided to the focusing device to shape the focus of the radiation rays, while the high voltage generator provides the tube voltage with a corresponding value to the radiation source at the same specific time point.

The focus of the radiation rays generated by the radiation source may satisfy an operational constraint when the tube voltage changes according to the first reference parameter after the focusing device shapes the focus of the radiation rays under the focusing parameter changing according to the second reference waveform. In some embodiments, the operational constraint may include that a size of the focus of radiation rays is in a range when the tube voltage changes according to the first reference waveform. The range may be from 0.5 millimeters×0.9 millimeters to 0.5 millimeters×1.0 millimeter, or from 0.5 millimeters×0.8 millimeters to 0.5 millimeters×1.0 millimeter, etc. In some embodiments, the operational constraint may include that a size of the focus of radiation rays is equal to a fixed value when the tube voltage changes according to the first reference waveform. The fixed value may be 0.5 millimeters×1.0 millimeter, or 1.0 millimeter×1.0 millimeter, etc.

The image generation module 540 may be configured to obtain projection data generated by detecting at least a portion of the radiation rays by one or more detectors of the radiation device. The projection data may indicate an attenuation (i.e., CT values) of at least a portion of the radiation rays passing through a subject.

In some embodiments, the projection data may include a first portion and a second portion. The first portion of the projection data may correspond to the high-energy projection. The second portion of the projection data may correspond to the low-energy projection. The image generation module 540 may use the first portion and the second portion of the projection data to generate and/or reconstruct one or more density images (e.g., a bone density image, a soft tissue density image, etc.) of the subject using an image reconstruction algorithm. In some embodiments, the image generation module 540 may designate multiple groups of weights to the first portion of the projection data and the second portion of the projection data. Each group of the multiple groups of weights may include a first weight to the first portion of the projection data and a second weight to the second portion of the projection data. The image generation module 540 may reconstruct a series of weighted average images using an image reconstruction algorithm by weighting the first portion of the projection data and the second portion of the projection using the first weight and the second weight, respectively. The image generation module 540 may reconstruct a high-energy image based on the first portion of the projection data and a low-energy image based on the second portion of the projection data using an image reconstruction algorithm. The image generation module 540 may perform a dual-energy analysis operation on the series of weighted average images, the high-energy image, and/or the low-energy image.

The storage module 550 may be configured to store data and/or instructions associated with the imaging system 100. For example, the storage module 450 may store data of the first reference waveform, the second reference waveform, the feedback of the tube voltage, etc. In some embodiments, the storage module 550 may be same as the storage device 130, the storage 320, and/or the storage 490 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the obtaining module 510 and the focusing parameter determination module 520 may be integrated into a single module. As another example, some other components/modules may be added into the processing device 120, e.g., a detection module.

Figure 6:
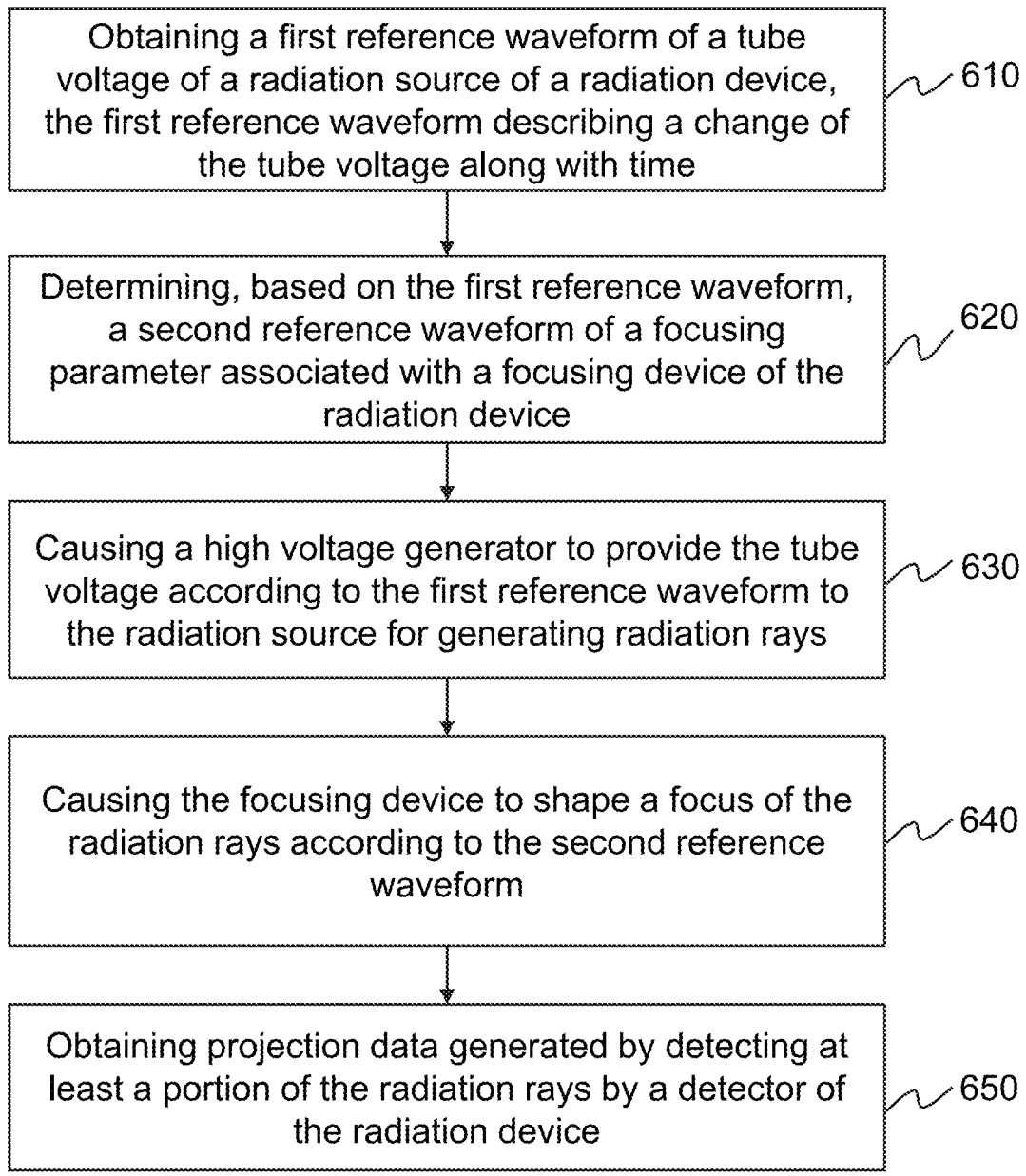
FIG. 6 is a schematic flowchart illustrating an exemplary process for energy imaging according to some embodiments of the present disclosure.

FIG. 6 is a schematic flowchart illustrating an exemplary process for energy imaging according to some embodiments of the present disclosure. In some embodiments, process 600 may be implemented as a set of instructions (e.g., an application) stored in the storage device 130, storage 320, or storage 490. The processing device 120, the processor 310 and/or the CPU 440 may execute the set of instructions, and when executing the instructions, the processing device 120, the processor 310 and/or the CPU 440 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of the process 600 illustrated in FIG. 6 and described below is not intended to be limiting.

In 610, the processing device 120 (e.g., the obtaining module 510) may obtain a first reference waveform of a tube voltage of a radiation source of a radiation device. The radiation device may include an imaging device, a treatment device, etc. In some embodiments, the radiation source (e.g., the imaging device) may include a tube, a high voltage generator, etc. The high voltage generator may be configured to provide the tube voltage for the tube. The tube may emit radiation rays (also referred to as radiation beams) based on the tube voltage. In some embodiments, the radiation rays may include X-rays, γ-rays, α-rays, or the like, or a combination thereof. More descriptions for the radiation source may be found elsewhere in the present disclosure (e.g., FIGS. 2A-2C and the descriptions thereof).

The first reference waveform may describe a change of the tube voltage with time. The first reference waveform may include a rectangular waveform, a trapezoidal waveform, a triangular waveform, a sinusoidal waveform, etc. The high voltage generator may provide the tube voltage to the radiation source according to the first reference waveform. For example, the high voltage generator may provide the tube voltage switching between a first voltage and a second voltage higher than the first voltage to the radiation source according to the first reference waveform in an energy imaging scan. The first voltage and the second voltage may be desired values of the tube voltage that the high voltage generator of the radiation device may provide to the tube the energy imaging scan is performed. The first voltage and/or the second voltage may be determined by an operator or according to a default setting of the imaging system 100. For example, the first voltage may be a value in a range from 70 kV to 100 kV, in a range from 80 kV to 100 kV, etc. The second voltage may be a value in a range from 120 kV to 150 kV, or in a range from 120 kV to 140 kV, etc.

In some embodiments, the first reference waveform may include a plurality of first points. Each of the plurality of first points may be defined by a time point and a value of the tube voltage corresponding to the time point. In some embodiments, the first reference waveform may include a plurality of first sections corresponding to different time periods according to the change of the tube voltage. For example, one of the plurality of first sections of the first reference waveform may describe that the tube voltage decreases from the second voltage to the first voltage, or increases from the first voltage to the second voltage, or is maintained at the first voltage, or is maintained at the second voltage, etc. As used herein, a first section of the first reference waveform describing that the tube voltage increases from the first voltage to the second voltage may be also referred to as a rising edge. A first section of the first reference waveform describing that the tube voltage decreases from the second voltage to the first voltage may be also referred to as a falling edge. A first section of the first reference waveform describing that the tube voltage is maintained at the first voltage may be also referred to as a platform stage of a low voltage. A first section of the first reference waveform describing that the tube voltage is maintained at the second voltage may be also referred to as a platform stage of a high voltage. In some embodiments, the first reference waveform may include a high-energy projection and a low-energy projection. As used herein, the high-energy projection may correspond to a transition of the tube voltage that varies between the second voltage and a half of the sum of the first voltage and the second voltage. The low-energy projection may refer to a transition of the tube voltage that varies between the first voltage and the half of the sum of the first voltage and the second voltage. In some embodiments, the first reference waveform may be periodic. A high-energy projection and a low-energy projection in one cycle may form an energy view.

Figure 8:
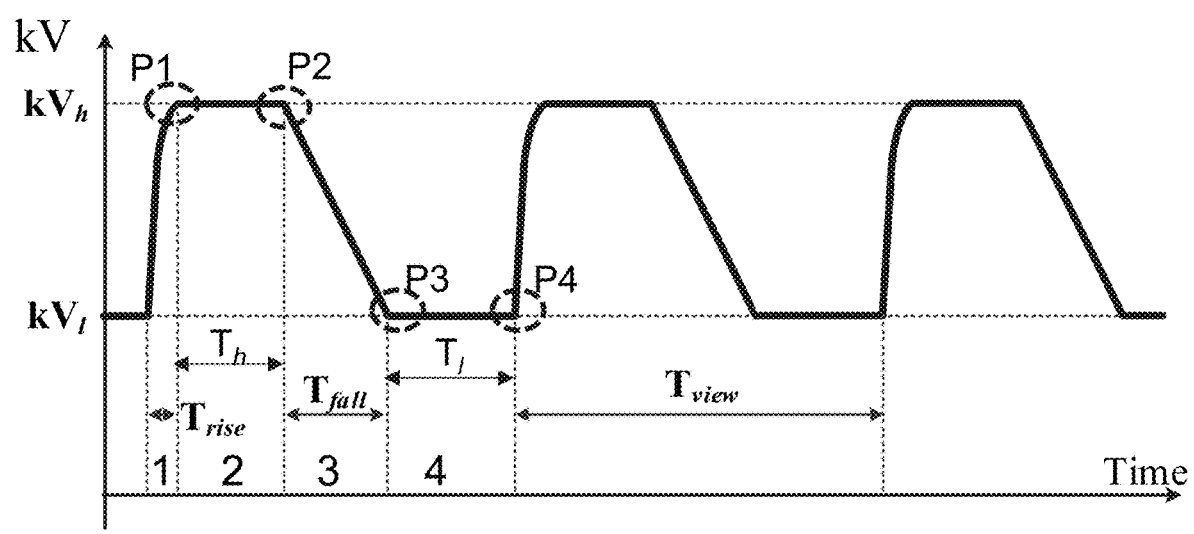
FIG. 8 is a diagram illustrating an exemplary reference waveform of a tube voltage according to some embodiments of the present disclosure.

In some embodiments, the first reference waveform may be defined by one or more switching parameters of the tube voltage. The one or more switching parameters may include the first voltage, the second voltage higher than the first voltage, a first time length (i.e., a transition time of the rising edge) that it takes for tube voltage to change from the first voltage to the second voltage, a second time length (i.e., a transition of the falling edge) that it takes for the tube voltage changes from the second voltage to the first voltage, a third time length that the tube voltage is maintained at the first voltage, a fourth time length that the tube is maintained at the second voltage, switching time points, or the like, or any combination thereof. As used herein, a switching time point may refer to a time point when the tube voltage starts to change from the first voltage to the second time point or from the second voltage to the first time point (e.g., points P1, P2, P3, P4, etc., illustrated in FIG. 8). A switching time point may be a starting time point or ending time point of a falling edge and/or a rising time point. For example, as shown in FIG. 8, the first reference waveform may include a first section 1 corresponding to a first time length $T_{rise}$ during which the tube voltage increases with time, a first section 2 corresponding to a fourth time length $T_h$ during which the tube voltage maintains at a high voltage $kV_h$, a first section 3 corresponding to a second time length $T_{fall}$ during which the tube voltage decreases with time, and a first section 4 corresponding to a third time length $T_l$ during which the tube voltage maintains at a low voltage $kV_l$.

In some embodiments, the processing device 120 may obtain the first reference waveform from the imaging device 110, the storage device 130, the terminal(s) 140, or any other storage device. For example, the first reference waveform may be determined by a processing device different from or same as the processing device 120 offline and stored in the storage device 130. In some embodiments, the first reference waveform of the tube voltage may be determined by an operator of the radiation source or according to a default setting of the imaging system 100. For example, the first reference waveform may be obtained from a database (e.g., the storage device 130) storing multiple first reference waveforms. Each of the multiple first reference waveforms may correspond to a scanning protocol. The processing device 120 may retrieve the first reference waveform from the database based on a specific scanning protocol. As another example, the first reference waveform may be determined by the operator via setting the switching parameters of the first reference waveform via the terminals 140. More descriptions regarding the first reference waveform of a tube voltage of a radiation source of a radiation device may be found in, for example, U.S. application Ser. No. 16/666,435, entitled "SYSTEMS AND METHODS FOR X-RAY IMAGING" filed on even date, the contents of which are hereby incorporated by reference.

In 620, the processing device 120 (e.g., the focusing parameter determination module 520) may determine a second reference waveform of a focusing parameter associated with a focusing device based on the first reference waveform. The focusing device may be configured to shape a focus of radiation rays generated by the radiation source. For example, the focusing device may control a size and/or a position/location of the focus of radiation rays. In some embodiments, the focusing device may be configured to shape the focus of the radiation rays generated by the radiation source by generating an electric field under a focusing voltage and the focusing parameter may include the focusing voltage. In some embodiments, the focusing device may be configured to shape the focus of the radiation rays generated by the radiation source by generating a magnetic field under a focusing current, and the focusing parameter includes the coil current. More descriptions for the focusing device may be found elsewhere in the present disclosure (e.g., FIGS. 2B and 2C, and the descriptions thereof).

The second reference waveform may describe a change of the focusing parameter with time when the tube voltage changes with time according to the first reference waveform. The focusing parameter (e.g., the focusing voltage or the coil current) may be provided to the focusing device according to the second reference waveform. For example, the focusing parameter switching between a minimum value and a maximum value higher than the minimum value may be provided to the focusing device according to the second reference waveform. The focusing device may shape the focus of the radiation rays in a specific desired size range or a desired specific size (e.g., 0.5 millimeters×1.0 millimeter) when the tube voltage changes with time according to the first reference waveform and the focusing parameter changes with time according to the second reference waveform, simultaneously.

Figure 10:
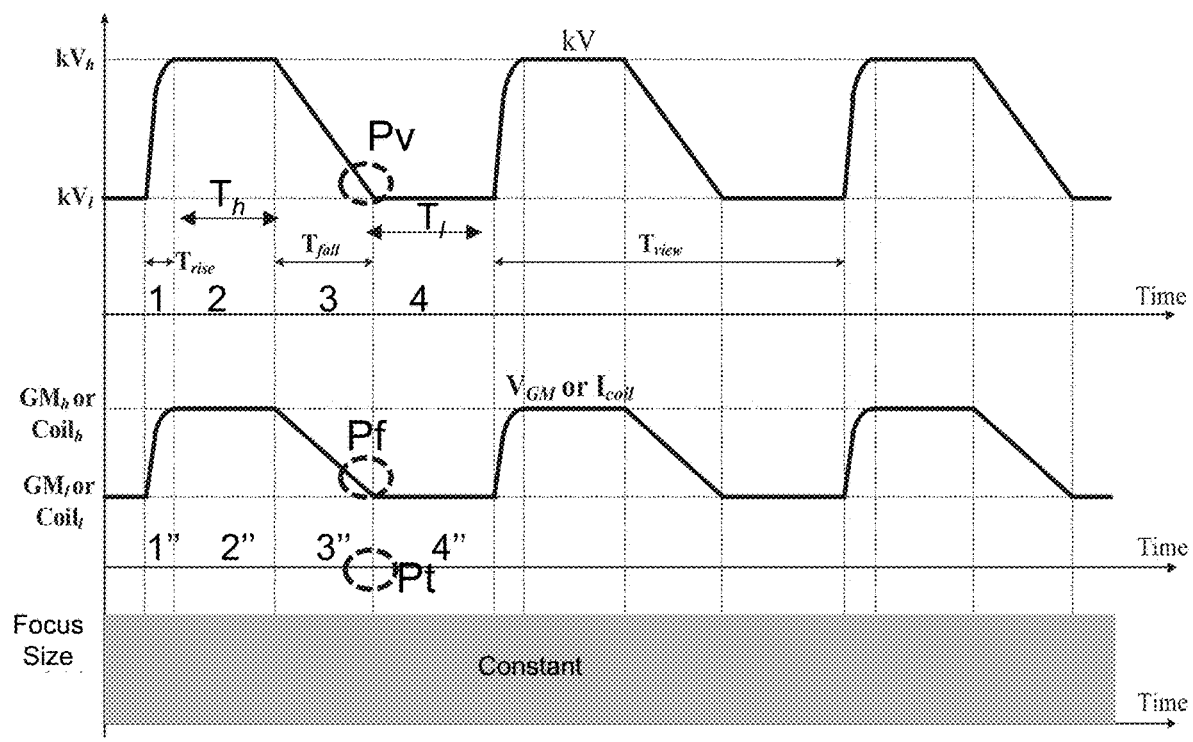
FIG. 10 is a diagram illustrating an exemplary waveform of a tube voltage and a waveform of a focusing parameter according to some embodiments of the present disclosure.

In some embodiments, the second reference waveform may include a plurality of second points. Each of the plurality of second points may be defined by a time point and a value of the focusing parameter (e.g., the focusing voltage, the focusing current). Each of the plurality of second points of the second reference waveform may correspond to one of the plurality of first points of the first reference waveform. As used herein, a second point corresponding to a first point may indicate that the second point and the first point correspond to a same time point. For example, as illustrated in FIG. 10, the point Pv of the first reference waveform may correspond to the point Pf of the second reference waveform. The point Pv of the first reference waveform and the point Pf of the second reference waveform may correspond to the same time point Pt.

In some embodiments, each of the plurality of second points may be determined based on the corresponding first point. For example, the processing device 120 may obtain a relationship between the tube voltage and the focusing parameter with respect to a specific size of the focus. The specific size of the focus may be equal to or close to the desired specific size (e.g., 0.5 millimeters×1.0 millimeter) of the focus. The relationship between the tube voltage and the focusing parameter may provide multiple groups of values or ranges of the tube voltage and values of the focusing parameter. Each group of the multiple groups may include a value or a range of the tube voltage and a corresponding value of the focusing parameter. In some embodiments, the relationship between the tube voltage and the focusing parameter may be stored in a database storing multiple relationships between the tube voltage and the focusing parameter. Each of the multiple relationships between the tube voltage and the focusing parameter may correspond to a size of the focus or a range of the size of the focus (e.g., 0.5×1.0 mm², 1.0×1.0 mm², 1.0×1.5 mm², etc.). The processing device 120 may retrieve the relationship between the tube voltage and the focusing parameter with respect to the specific size of the focus from the database. The processing device 120 may determine a value of the focusing parameter corresponding to a specific second point based on the relationship and a value of the tube voltage corresponding to the specific first point. In some embodiments, the relationship between the tube voltage and the focusing parameter with respect to a size of the focus may be denoted as a table. In some embodiments, the relationship between the tube voltage and the focusing parameter with respect to a size of the focus may be denoted as a function or model. The function or model may be used to generate a value of the focusing parameter based on a value of the tube voltage.

In some embodiments, the second reference waveform may include a plurality of second sections corresponding to different time periods. Each of the plurality of second sections may correspond to one of the plurality of the first sections of the first reference waveform. A second section corresponding to a first section may indicate that the second section and the first section correspond to a same time period. For example, one of the plurality of first sections of the first reference waveform may describe that the focusing parameter decreases from the maximum value to the minimum value, or increase from the minimum value to the maximum value, or be maintained at the maximum value, or be maintained at the minimum value, etc. As used herein, a second section of the second reference waveform describing that the focusing parameter increases from the minimum value to the maximum value may be also referred to as a rising edge of the second reference waveform. A second section of the second reference waveform describing that the focusing parameter decreases from the maximum value to the minimum value may be also referred to as a falling edge of the second reference waveform. A second section of the second reference waveform describing that the focusing parameter is maintained at the minimum value may be also referred to as a low-parameter platform stage of the second reference waveform. A second section of the second reference waveform describing that the focusing parameter is maintained at the maximum value may be also referred to as a high-parameter platform stage.

In some embodiments, the processing device 120 may determine the second reference waveform based on the switching parameters of the first reference waveform. Further, the processing device 120 may determine each of the plurality of second sections based on the one or more switching parameters of the tube voltage associated with the corresponding first section. For example, the processing device 120 may determine the minimum value of the focusing parameter based on the first voltage and determine the maximum value of the focusing parameter based on the second voltage according to the relationship between the focusing parameter and the tube voltage with respect to a specific size of the focus. The processing device 120 may determine a low-parameter platform stage of the second reference waveform based on the minimum value of the focusing parameter and the third time length that the tube voltage is maintained at the first voltage. The processing device 120 may determine a high-parameter platform stage of the second reference waveform based on the maximum value of the focusing parameter and the fourth time length that the tube voltage is maintained at the second voltage. The processing device 120 may determine a first changing rate of the focusing parameter changing from the minimum value to the maximum value based on the first time length it takes for the tube voltage to change from the first voltage to the second voltage. As used herein, the first changing rate may refer to an average speed of the focusing parameter changing from the minimum value to the maximum value. The processing device 120 may determine the rising edge of the second reference waveform based on the first changing rate and the first time length it takes for the tube voltage changes from the first voltage to the second voltage. The processing device 120 may determine a second changing rate of the focusing parameter changing from the maximum value to the minimum value based on the second time of duration. As used herein, the second changing rate may refer to an average speed of the focusing parameter changing from the maximum value to the minimum value. The processing device 120 may determine the falling edge of the second reference waveform based on the second changing rate and the second time length it takes for the tube voltage changes from the second voltage to the first voltage. The first changing rate and the second changing rate may be also referred to as a slope of the rising edge and the falling edge of the second reference waveform, respectively. For example, the minimum value may be denoted by x, the maximum value may be denoted by y, the first time length may be denoted by $t_1$, and the second time length may be denoted by $t_2$, the first changing rate of the focusing parameter may be determined as $$k_1 = \frac{y - x}{t_1}$$

and the second changing rate of the focusing parameter may be determined as $$k_2 = \frac{x - y}{t_2}.$$

The processing device 120 may determine the second reference waveform based on the determined falling edge, the determined rising edge, the determined low-parameter platform stage, and the determined high-parameter platform stage.

In some embodiments, the processing device 120 may determine a rising edge and/or a falling edge of the second reference waveform by determining multiple changing rates of the focusing parameter in the first time length and/or the second time length. For example, the processing device 120 may determine multiple values of the tube voltage corresponding to multiple time points during the first time length. The processing device 120 may determine multiple values of the focusing parameter corresponding to the multiple time points based on the multiple values of the tube voltage during the first time length. Each of the multiple values of the focusing parameter may correspond to one of the multiple values of the tube voltage. The multiple values of the focusing parameter may be between the minimum value and the maximum value. The processing device 120 may determine a first changing rate of the focusing parameter between two consecutive time points based on values of the focusing parameter corresponding to the two consecutive time points. Then the processing device 120 may determine a rising edge of the second reference waveform based on the plurality of first changing rates. Accordingly, the processing device 120 may determine a falling edge of the second reference waveform as described above.

In 630, the processing device 120 (e.g., the control module 530) may cause the high voltage generator to provide the tube voltage according to the first reference waveform to the radiation source for generating radiation rays.

In some embodiments, the processing device 120 may transmit the first reference waveform in the form of instructions to the controller of the high voltage generator. The controller of the high voltage generator may cause the high voltage generator to generate the tube voltage according to the first reference waveform in response to the receipt of an exposure instruction from the processing device 120 or the terminal 140. The tube voltage provided by the high voltage generator to the radiation source may switch between the first voltage (i.e., a high voltage) and the second voltage (i.e., a low voltage). The radiation source may generate the radiation rays under the tube voltage switching rapidly between the high voltage and the low voltage for energy imaging. The high voltage generator may supply the generated tube voltage with actual values between an anode and the cathode of the tube. An electric field may be generated between the anode and the cathode of the tube as the tube voltage provided by the high voltage generator. In some embodiments, the high voltage generator may also supply a current to a cathode filament of the tube for heating the cathode filament to generate hot electrons. The hot electrons may impinge an anode target under the electric field between the anode and the cathode to generate radiation rays (e.g., X-rays).

In 640, the processing device 120 (e.g., the control module 530) may cause the focusing device to shape a focus of the radiation rays according to the second reference waveform. In some embodiments, the processing device 120 may transmit the second reference waveform in the form of instructions to a controller of the focusing device. The controller of the focusing device may control a power to provide the focusing parameter (e.g., a focusing voltage, a focusing current) with specific values according to the second reference waveform in response to the receipt of an exposure instruction from the processing device 120 or the terminal 140. The focusing parameter with a specific value at a specific time point may be provided to the focusing device to shape the focus of the radiation rays, while the high voltage generator provides the tube voltage with a corresponding value to the radiation source at the same specific time point.

The focus of the radiation rays generated by the radiation source may satisfy an operational constraint when the tube voltage changes according to the first reference parameter after the focusing device shapes the focus of the radiation rays under the focusing parameter changing according to the second reference waveform. In some embodiments, the operational constraint may include that a size of the focus of radiation rays is in a range when the tube voltage changes according to the first reference waveform. The range may be from 0.5 millimeters×0.9 millimeters to 0.5 millimeters×1.0 millimeter, or from 0.5 millimeters×0.8 millimeters to 0.5 millimeters×1.0 millimeter, etc. In some embodiments, the operational constraint may include that a size of the focus of radiation rays is equal to a fixed value when the tube voltage changes according to the first reference waveform. The fixed value may be 0.5 millimeters×1.0 millimeter, or 1.0 millimeter×1.0 millimeter, etc.

In some embodiments, the processing device 120 may transmit the second reference waveform in the form of instructions to a controller of the focusing device. The controller of the focusing device may be the same as or different from the controller of the high voltage generator. The controller may control a power associated with the focusing device to provide the focusing parameter (e.g., the focusing voltage, the focusing current) changing according to the second reference waveform to the focusing device according to the instructions. In some embodiments, the power may be the high voltage generator. In some embodiments, the power may be separated physically from the high voltage generator. The controller of the focusing device may adjust the focusing parameter of the focusing device according to the second reference waveform in response to the receipt of an exposure instruction from the processing device 120 or the terminal 140.

In 650, the processing device 120 (e.g., the detection module 540) may obtain projection data generated by detecting at least a portion of the radiation rays by one or more detectors of the radiation device.

In some embodiments, one or more detectors may absorb the energy of the at least a portion of the generated radiation rays (e.g., X rays) when the at least a portion of the radiation rays (e.g., γ ray) impinge on the one or more detectors. The one or more detectors may convert the absorbed energy into visible light signals. Further, the one or more detectors may convert the visible light signals into electrical signals (i.e., the projection data). The projection data may indicate an attenuation (i.e., CT values) of at least a portion of the radiation rays passing through the subject. In some embodiments, the projection data may include a first portion and a second portion. The first portion of the projection data may correspond to the high-energy projection as described in operation 610. The first portion of the projection data corresponding to the high-energy projection may refer to that the first portion of the projection data may be generated by the one or more detectors via receiving radiation rays corresponding to the high-energy spectrum. The second portion of the projection data may correspond to the low-energy projection. The second portion of the projection data corresponding to the low-energy projection may refer to that the second portion of the projection data may be generated by the one or more detectors via receiving radiation rays corresponding to the low-energy spectrum.

The first portion and the second portion of the projection data may be used in a multi-energy spectral imaging technique, such as a dual-energy subtraction technique, etc. For example, the projection data may be used to generate and/or reconstruct one or more density images (e.g., a bone density image, a soft tissue density image, etc.) of the subject using an image reconstruction algorithm. As another example, the processing device 120 may designate multiple groups of weights to the first portion of the projection data and the second portion of the projection data. Each group of the multiple groups of weights may include a first weight to the first portion of the projection data and a second weight to the second portion of the projection data. The processing device 120 may reconstruct a series of weighted average images using an image reconstruction algorithm by weighting the first portion of the projection data and the second portion of the projection using the first weight and the second weight, respectively. The processing device 120 may reconstruct a high-energy image based on the first portion of the projection data and a low-energy image based on the second portion of the projection data using an image reconstruction algorithm. The processing device 120 may perform a dual-energy analysis operation on the series of weighted average images, the high-energy image, and/or the low-energy image. In some embodiments, the dual-energy analysis operation may include using an image optimization algorithm, a non-linear blending algorithm, etc., to obtain one or more monoenergetic images. In some embodiments, the dual-energy analysis operation may include using a differentiation algorithm to identify or differentiate certain materials or substances of the subject. In some embodiments, the dual-energy analysis operation may include using a quantification algorithm to quantify one or more substances of the subject. Exemplary image reconstruction algorithms may include using an iterative reconstruction model, a Fourier slice theorem model, a fan-beam reconstruction model, an analytic reconstruction model, an algebraic reconstruction technique (ART), a simultaneous algebra reconstruction technique (SART), a Feldkamp-Davis-Kress (FDK) reconstruction model, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, the operation 630 and the operation 640 may be combined into a single operation to cause the radiation device to produce radiation rays with a small focus. As another example, one or more other optional operations (e.g., a storing operation) may be added elsewhere in the process 600. In the storing operation, the processing device 120 may store information and/or data (e.g., the first reference waveform, the second reference waveform, the projection data, etc.) associated with the imaging system 100 in a storage device (e.g., the storage device 130) disclosed elsewhere in the present disclosure. As still another example, operation 630 and/or 650 may be omitted.

Figure 7:
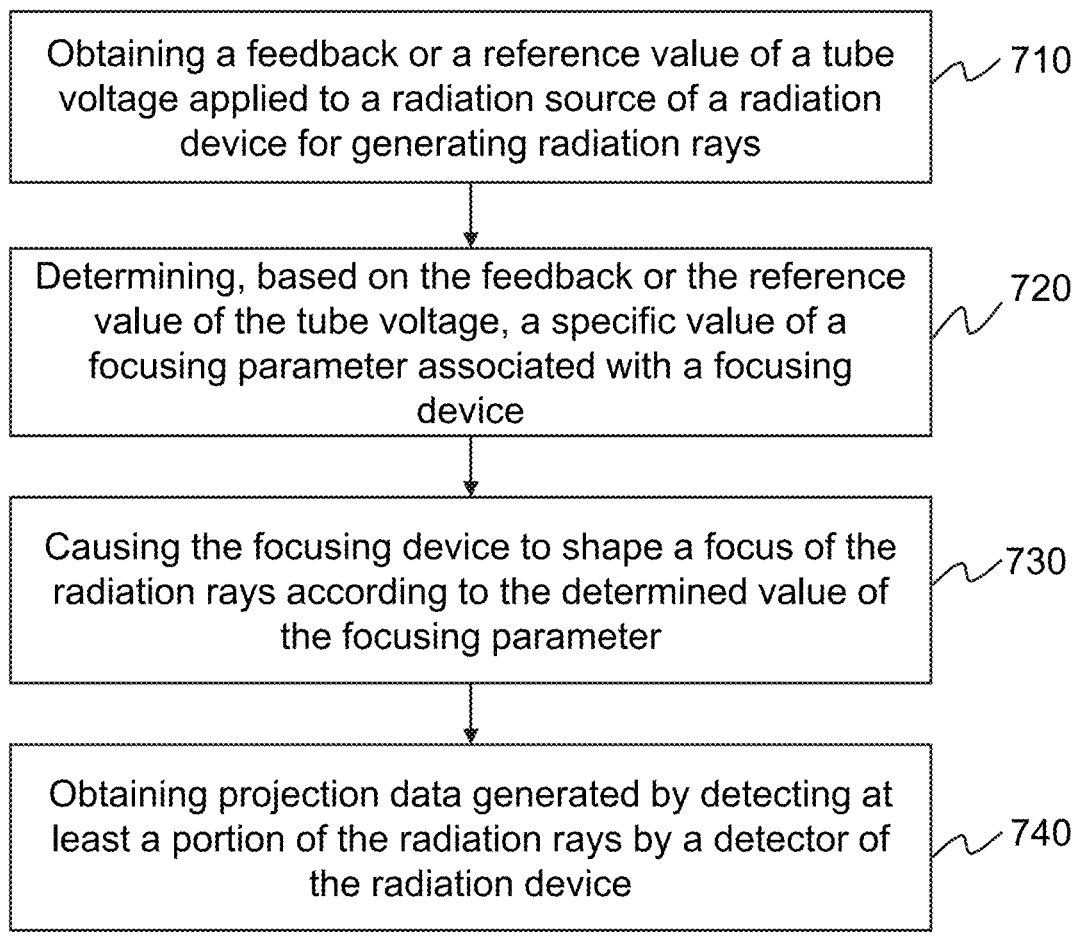
FIG. 7 is a schematic flowchart illustrating an exemplary process for energy imaging according to some embodiments of the present disclosure.

FIG. 7 is a schematic flowchart illustrating an exemplary process for energy imaging according to some embodiments of the present disclosure. In some embodiments, process 700 may be implemented as a set of instructions (e.g., an application) stored in the storage device 130, storage 320, or storage 490. The processing device 120, the processor 310 and/or the CPU 440 may execute the set of instructions, and when executing the instructions, the processing device 120, the processor 310 and/or the CPU 440 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of the process 700 illustrated in FIG. 6 and described below is not intended to be limiting.

In 710, the processing device 120 (e.g., the obtaining module 510) may obtain in real time a feedback or the reference value of a tube voltage applied to a radiation source of a radiation device for generating radiation rays. The radiation device may include an imaging device, a treatment device, etc. In some embodiments, the radiation source (e.g., the imaging device) may include a tube, a high voltage generator, etc. The high voltage generator may be configured to provide the tube voltage for the tube. The tube may emit radiation rays (also referred to as radiation beams) based on the tube voltage. In some embodiments, the radiation rays may include X-rays, γ-rays, α-rays, or the like, or a combination thereof. More descriptions for the radiation source may be found elsewhere in the present disclosure (e.g., FIGS. 2A-2C and the descriptions thereof).

The feedback of the tube voltage may include at least one of an actual value of the tube voltage that the high voltage generator generates and provides to the tube in a procedure using the radiation rays, such as an imaging procedure, a treatment procedure, etc., and the time point when the actual value of the tube voltage is obtained. The reference value of the tube voltage may be stored in the form of instructions to a controller of the high voltage generator. In some embodiments, the reference value of the tube voltage may be obtained based on a reference waveform of the tube voltage (e.g., the first reference waveform as described in FIG. 6). In some embodiments, the feedback and/or the reference value of the tube voltage may be acquired and/or collected by a controller of the high voltage generator. The processing device 120 may obtain the feedback and/or the reference value of the tube voltage from the controller of the high voltage generator. For example, the controller of the high voltage generator may use a closed-loop control technique (e.g., a proportion-integral-differential (PID) controller to track and/or collect in real time the feedback of the tube voltage. The controller of the high voltage generator may transmit the collected feedback of the tube voltage to the processing device 120. In some embodiments, the feedback of the tube voltage may be acquired and/or collected in real time by a voltage sensor. The processing device 120 may obtain the feedback of the tube voltage from the voltage sensor. The voltage sensor may include a voltage transformer, a Hall voltage sensor, an optical fiber voltage sensor, etc. As used herein, the obtaining in real time the feedback (or the reference value) of the tube voltage may refer to that the feedback (or the reference value) of the tube voltage may be collected and/or sampled at an acquisition frequency (also referred to as an acquisition speed or sampling frequency) and transmitted to the processing device 120 when (or before) the tube voltage is generated by the high voltage generator. The controller of the high voltage generator or the voltage sensor, etc., may collect in real time the feedback (or the reference value) of the tube voltage according to the acquisition frequency and transmit the collected feedback of the tube voltage to the processing device 120. The acquisition frequency may be set by an operator or according to a default setting of the imaging system 100. For example, the controller of the high voltage generator or the voltage sensor, etc., may collect the feedback of the tube voltage 20 times in 100 microseconds. As another example, the controller of the high voltage generator or the voltage sensor, etc., may collect the feedback (or the reference value) of the tube voltage every 1 microsecond, or 2 microseconds, or 5 microseconds, or 10 microseconds, etc. In some embodiments, the controller of the high voltage generator, the voltage sensor, etc., may collect the feedback (or the reference value) of the tube voltage at multiple time points. The multiple time points may be defined by a starting time point when the high voltage generator generates the tube voltage. For example, if the starting time point when the high voltage generator generates the tube voltage is defined as 0 microseconds, the multiple time points may include 0 microseconds, 5 microseconds, 10 microseconds, 15 microseconds, etc. The controller of the high voltage generator, the voltage sensor, etc., may collect the feedback of the tube voltage at 0 microseconds, 5 microseconds, 10 microseconds, 15 microseconds, etc., respectively, and transmit the collected feedback of the tube voltage to the processing device 120. The sampling frequency or speed of the feedback of the tube voltage may be set by an operator or according to a default setting of the imaging system 100. For example, the sampling frequency or speed of the feedback of the tube voltage may be lower than the sampling speed of imaging data (i.e., projection data).

In 720, the processing device 120 (e.g., the focusing parameter determination module 520) may determine a specific value of a focusing parameter associated with a focusing device based on the feedback or the reference value of the tube voltage. The focusing device may be configured to shape a focus of radiation rays generated by the radiation source. For example, the focusing device may control a size and/or a position/location of the focus of radiation rays. In some embodiments, the focusing device may be configured to shape the focus of the radiation rays generated by the radiation source by generating an electric field under a focusing voltage and the focusing parameter may include the focusing voltage. In some embodiments, the focusing device may be configured to shape the focus of the radiation rays generated by the radiation source by generating a magnetic field under a focusing current, and the focusing parameter includes the coil current. More descriptions for the focusing device may be found elsewhere in the present disclosure (e.g., FIGS. 2B and 2C, and the descriptions thereof).

In some embodiments, the processing device 120 may obtain a relationship between the tube voltage and the focusing parameter with respect to a specific size of a focus or a specific range of the size of the focus. The processing device 120 may determine the specific value of the focusing parameter based on the feedback (or the reference value) of the tube voltage and the relationship. The actual size of the focus of the radiation rays generated by the tube when the tube is applied with the tube voltage and shaped by the focusing device under the focusing parameter may be same as or close to the specific size of the focus or in the specific range of the size of the focus if values of the tube voltage and values of the focusing parameter satisfy the relationship. The specific size of the focus may include a fixed size of an actual focus and/or a fixed size of an effective focus as described elsewhere in the present disclosure (e.g., FIG. 6 and the descriptions thereof). As used herein, a first value (e.g., the actual size of the focus) same as or close to a second value (e.g., the specific size of the focus) may indicate that the deviation between the first value and the second value is less than 3%, or 2%, or 1%, or 0.5%, or 0.1%, etc.

In some embodiments, the relationship between the tube voltage and the focusing parameter may provide multiple groups of values of the tube voltage and the focusing parameter. Each group of the multiple groups of values of the tube voltage and the focusing parameter may include a value of the tube voltage and a corresponding value of the focusing parameter. As used herein, the relationship providing multiple groups of values of the tube voltage and the focusing parameter may be also referred to as a first relationship. The processing device 120 may determine the specific value of the focusing parameter corresponding to the feedback of the tube voltage based on the first relationship. For example, when the specific size of the focus corresponding to the first relationship is 0.5×1.0 mm², and the focusing parameter is a focusing voltage, the first relationship between the tube voltage and the focusing parameter may be denoted as 80 kV (the tube voltage)—−900V (the focusing voltage), 100 kV (the tube voltage)—−1090 V (the focusing voltage), 120 kV (the tube voltage)—−1290 V (the focusing voltage), etc. If the feedback (or the reference value) of the tube voltage is 80 kV, the processing device 120 may determine that the specific value of the focusing parameter corresponding to the feedback (or the reference value) of the tube voltage is −900V.

In some embodiments, the relationship between the tube voltage and the focusing parameter may provide multiple groups of ranges of the tube voltage and values of the focusing parameter. Each group of the multiple groups of ranges of the tube voltage and the focusing parameter may include a range of the tube voltage and a corresponding value of the focusing parameter. As used herein, the relationship providing multiple groups of ranges of the tube voltage and the focusing parameter may be also referred to as a second relationship. The processing device 120 may determine the specific value of the focusing parameter corresponding to the feedback (or the reference value) of the tube voltage based on the second relationship and the feedback (or the reference value) of the tube voltage. For example, the processing device 120 may determine a specific range of the tube voltage where the feedback (or the reference value) of the tube voltage belongs to. The processing device 120 may determine the specific value of the focusing parameter corresponding to the feedback (or the reference value) of the tube voltage based on the second relationship and the specific range of the tube voltage. As a further example, when the focusing parameter is a focusing voltage, the feedback (or the reference value) of the tube voltage is 85 kV, the second relationship with respect to the specific range of the size of the focus may be denoted as [80 kV, 90 kV) (the tube voltage)—−950V (the focusing voltage), [90 kV, 100 kV) (the tube voltage)—−1050 V (the focusing voltage), [100 kV, 110 kV) (the tube voltage)—−1150 V (the focusing voltage), etc. The processing device 120 may determine the feedback (or the reference value) 85 kV belongs to [80 kV, 90 kV). Then the focusing parameter may be determined as −950 kV.

In some embodiments, the relationship between the tube voltage and the focusing parameter may include a first portion corresponding to a rising edge that the tube voltage increases from a low voltage (i.e., the first voltage) to a high voltage (i.e., the second voltage) and a second portion corresponding to a falling edge that the tube voltage decreases from the high voltage (i.e., the second voltage) to the low voltage (i.e., the first voltage). The same feedback (or the reference value) of the tube voltage may correspond to different values of the focusing parameters. In some embodiments, the processing device 120 may determine whether the tube voltage obtained in real time belongs to the falling edge or the rising edge. In some embodiments, the processing device 120 may determine whether the tube voltage obtained in real time belongs to the falling edge or the rising edge based on a changing rate of the tube voltage between two adjacent sampling points (or time points). The changing rate of the tube voltage may be determined based on the feedback of the tube voltage at the current time point or sampling point and a feedback of the tube voltage obtained at the last time point before the current time point. For example, if the feedback of the tube voltage obtained at the current time point is x, the feedback of the tube voltage obtained at the last time point is y, the changing rate may be determined as $$k = \frac{x-y}{\Delta t},$$

wherein Δt may refer to a time difference between the current time point and the last time point. The changing rate k may be positive when x is greater than y, and k may be negative when y is greater than x. The changing rate being positive may denote that the tube voltage is in the rising edge and the changing rate being negative may denote that the tube voltage is in the falling edge. The processing device 120 may determine the specific value of the focusing parameter corresponding to the feedback of the tube voltage based on the relationship between the tube voltage and the focusing parameter and the changing rate of the tube voltage at the current time point. The values of the focusing parameter corresponding to a same range or value of the tube voltage in the rising edge and the falling edge may be different. For example, when the tube voltage at the current time point is in the rising edge, the second relationship may be {[80 kV, 90 kV) (the tube voltage)—-950V (the focusing voltage)}, {[90 kV, 100 kV) (the tube voltage)—-1050 V (the focusing voltage)}, {[100 kV, 110 kV) (the tube voltage)—-1150 V (the focusing voltage)}, etc., and when the tube voltage is in the falling edge, the second relationship may be {[80 kV, 90 kV) (the tube voltage)—-900V (the focusing voltage)}, {[90 kV, 100 kV) (the tube voltage)—-950 V (the focusing voltage)}, {[100 kV, 110 kV) (the tube voltage)—-1050 V (the focusing voltage)}, etc.

In some embodiments, the relationship between the tube voltage and the focusing parameter may be denoted as a table. The table may include the multiple groups of values or ranges of the tube voltage and the focusing parameter. In some embodiments, the relationship between the tube voltage and the focusing parameter may be denoted as a function with the tube voltage as a dependent variable and the focusing parameter as an independent variable. The processing device 120 may obtain the relationship between the tube voltage and the focusing parameter from a database. For example, the database may store multiple relationships between the tube voltage and the focusing parameter corresponding to multiple sizes of the focus of radiation rays. Each of the multiple relationships between the tube voltage and the focusing parameter may correspond to assize of the focus of radiation rays. The processing device 120 may retrieve the relationship with respect to the specific size of focus from the database according to a desired size of the focus of radiation rays. The multiple relationships between the tube voltage and the focusing parameter may be obtained according to multiple experiments, clinical applications, or a simulation technique (e.g., Monte Carlo simulation technique).

In some embodiments, the processing device 120 may determine the specific value of the focusing parameter based on a current time point of the feedback of the tube voltage and a relationship between a time point and the focusing parameter, also referred to as a third relationship. For example, the processing device 120 may determine a changing rate of the focusing parameter in the falling edge and/or the rising edge of the tube voltage. The processing device 120 may determine the third relationship based on the changing rate of the focusing parameter in the falling edge and/or the rising edge of the tube voltage. The changing rate of the focusing parameter in the falling edge and/or the rising edge of the tube voltage may be determined as described in 620 in FIG. 6. If the processing device 120 determines that the tube voltage at the current time point is in the rising edge or the falling edge, the processing device 120 may determine the specific value of the focusing parameter based on the third relationship and the current time point.

In 730, the processing device 120 (e.g., the control module 530) may cause the focusing device to shape a focus of the radiation rays according to the determined value of the focusing parameter.

In some embodiments, the processing device 120 may transmit the specific value of the focusing parameter in the form of instructions to a controller of the focusing device. The controller of the focusing device may control a power to provide the focusing parameter (e.g., a focusing voltage, a focusing current) with the specific value.

The focus of the radiation rays generated by the radiation source may satisfy an operational constraint when the tube voltage changes after the focusing device shapes the focus of the radiation rays under the focusing parameter with the specific value determined based on feedbacks of the tube voltage In some embodiments, the operational constraint may include that a size of the focus of radiation rays is in a range when the tube voltage changes according to the first reference waveform. The range may be from 0.5 millimeters×0.9 millimeters to 0.5 millimeters×1.0 millimeter, or from 0.5 millimeters×0.8 millimeters to 0.5 millimeters×1.0 millimeter, etc. In some embodiments, the operational constraint may include that a size of the focus of radiation rays is equal to a fixed value when the tube voltage changes according to the first reference waveform. The fixed value may be 0.5 millimeters×1.0 millimeter, or 1.0 millimeter× 1.0 millimeter, etc.

In 740, the processing device 120 (e.g., the detection module 540) may obtain projection data generated by detecting at least a portion of the radiation rays by a detector of the radiation device.

In some embodiments, one or more detectors may absorb the energy of the at least a portion of the generated radiation rays (e.g., X rays) when the at least a portion of the radiation rays (e.g., γ ray) impinge on the one or more detectors. The one or more detectors may convert the absorbed energy into visible light signals. Further, the one or more detectors may convert the visible light signals into electrical signals (i.e., the projection data). The projection data may indicate an attenuation (i.e., CT values) of at least a portion of the radiation rays passing through the subject. More descriptions for the projection data may be found as described in operation 650 in FIG. 6.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, the operation 620 and the operation 630 may be combined into a single operation to shape a focus of the radiation rays. As another example, one or more other optional operations (e.g., a storing operation) may be added elsewhere in the process 600. In the storing operation, the processing device 120 may store information and/or data (e.g., the specific focusing parameter, the projection data, etc.) associated with the imaging system 100 in a storage device (e.g., the storage device 130) disclosed elsewhere in the present disclosure.

EXAMPLES

The examples are provided for illustration purposes, and not intended to limit the scope of the present disclosure.

Example 1 Exemplary Curve of a Tube Voltage Varying with Time

FIG. 8 is a diagram illustrating an exemplary reference waveform of a tube voltage according to some embodiments of the present disclosure. The reference waveform (e.g., the first reference waveform as described in FIG. 6) includes a first voltage $kV_l$, a second voltage $kV_h$ higher than the first voltage $kV_l$, a first time length $T_{rise}$ that it takes for the tube voltage to change from $kV_l$ to $kV_h$, a second time length $T_{fall}$ that it takes for the tube voltage to change from the $kV_h$ to $kV_l$, a third time length TI that the tube voltage maintains at $kV_l$, a fourth time length $T_h$ that the tube voltage maintains at $kV_h$, and one or more switching time points, such as points P1, P2, P3, etc. The first time length, the second time length, the third time length, and the fourth time length may consist a switching cycle $T_{view}$. As shown in FIG. 8, the switching of the tube voltage between a high voltage and a low voltage may include a transition time, for example, from the high voltage to the low voltage. The declining of the tube voltage from the high voltage to the low voltage may be realized based on the discharge of an output capacitance and a cable capacitance of a high voltage generator. A declining speed that the tube voltage decreases from the high voltage to the low voltage may be determined based on a tube current. The smaller the tube current is, the smaller the declining speed that the tube voltage decreases from the high voltage to the low voltage may be. For example, if the output capacitance of the high voltage generator is 1 nF and the tube current is 200 mA, the transition time that it takes for the tube voltage to decrease from the high voltage to the low voltage is about 300 microseconds. And, a fast tube current modulation technique may be used in an energy imaging technique, which may further increase the transition time that it takes for the tube voltage to decrease from the high voltage to the low voltage. Therefore, the focusing parameter of the focusing device needs to adjust based on the change of the tube voltage according to processes 600 or 700.

Figure 9:
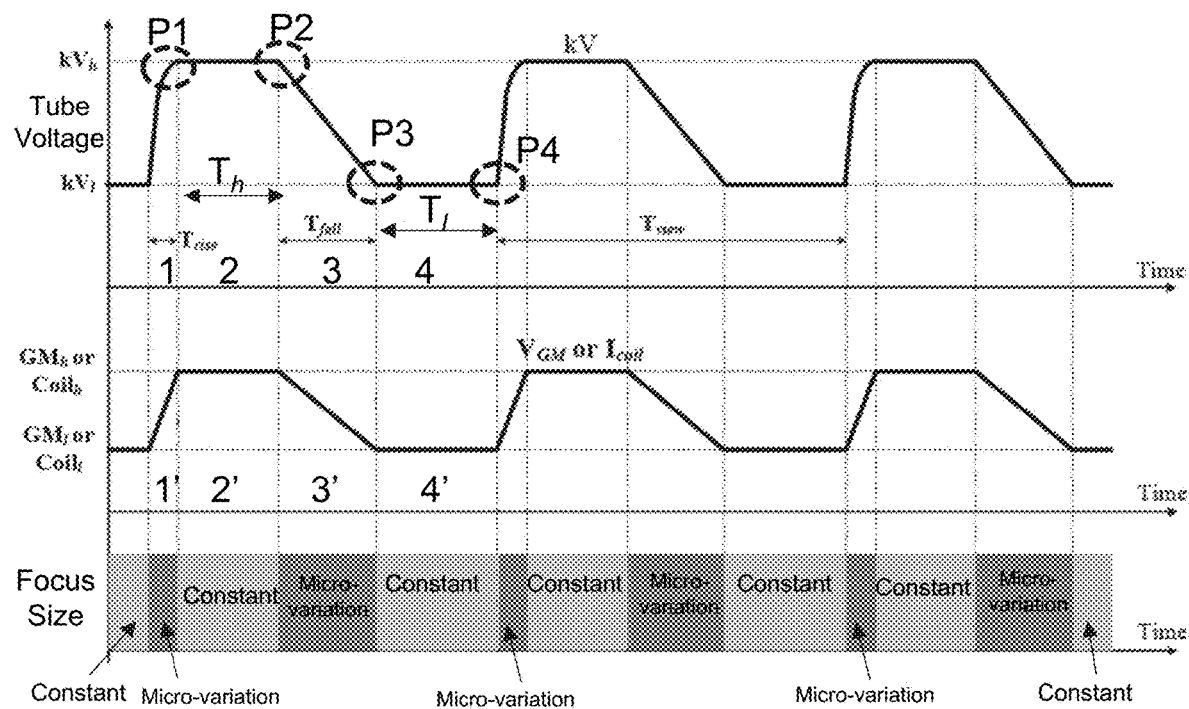
FIG. 9 is a diagram illustrating an exemplary waveform of a tube voltage and a waveform of a focusing current according to some embodiments of the present disclosure.

Example 2 Exemplary Curves of a Tube Voltage and a Focusing Current Varying with Time FIG. 9 is a diagram illustrating an exemplary waveform of a tube voltage and a waveform of a focusing current according to some embodiments of the present disclosure. As shown in FIG. 9, a first reference waveform of a tube voltage may be periodic. In one cycle, the first reference waveform may include a first section 1 (i.e., a rising edge) corresponding to a first transition time $T_{rise}$ (i.e., first time length) that it takes for the tube voltage to increase from a low voltage $kV_l$ to a high voltage $kV_h$, a first section 2 (i.e., a platform stage for the high voltage) corresponding to a fourth time length $T_h$ that the tube voltage is maintained at the high voltage $kV_h$, a first section 3 (i.e., a falling edge) corresponding to a second transition time $T_{fall}$ (i.e., second time length) that it takes for the tube voltage to decrease from the high voltage $kV_h$ to the low voltage $kV_l$, and a first section 4 (i.e., a platform stage for the low voltage) corresponding to a third time length $T_l$ that the tube voltage maintains at the low voltage $kV_l$. The fourth time length $T_h$ may be defined by point P1 and point P2. The third time length $T_l$ may be defined by point P3 and point P4. The first transition time $T_{rise}$ and the second transition time $T_{fall}$ may determine based on time points of the first reference waveform. A fixed rising rate (i.e., a slope of the rising edge of the first reference waveform) of the tube voltage may be determined based on the high voltage, the low voltage, and the first transition time $T_{rise}$. A fixed declining rate (i.e., a slope of the declining edge of the first reference waveform) of the tube voltage may be determined based on the high voltage, the low voltage, and the second transition time $T_{fall}$.

A second reference waveform of a focusing parameter (e.g., a focusing current denoted by denoted $I_{coil}$ or a focusing current denoted by denoted $V_{GM}$) may be determined as described according to process 600. The second reference waveform of the focusing parameter may be periodic. In one cycle, the second waveform of the focusing current or the focusing voltage may include a second section 1' (i.e., a rising edge) corresponding to the first transition time $T_{rise}$, a second section 2' corresponding to the fourth time length $T_h$, a second section 3' (i.e., a falling edge) corresponding to the second transition time $T_{fall}$, and a second section 4' corresponding to the third time length $T_l$. A first value (i.e., a minimum value) (e.g., $GM_l$ or $Coil_l$) of the focusing parameter may correspond to the low voltage $kV_l$. A second value (i.e., a maximum value) (e.g., $GM_h$ or $Coil_h$) of the focusing parameter may correspond to the high voltage $kV_h$. When the tube voltage changes in the rising edge (i.e., the first section 1) of the first reference waveform, the focusing parameter may increase from the first value to the second value to form a rising edge (i.e., the second section 1') of the second reference waveform according to a fixed rising rate. The fixed rising rate (i.e., a slope of the rising edge of the second reference waveform) may be determined based on the first value, the second value, and the first transition time $T_{rise}$. When the tube voltage is maintained at the high voltage (i.e., the first section 2), the focusing parameter may be maintained at the second value (i.e., the second section 2'). When the tube voltage changes in the falling edge (i.e., the first section 3) of the first reference waveform, the focusing parameter may decrease from the second value to the first value to form a falling edge (i.e., the second section 3') of the second reference waveform according to a fixed declining rate. The fixed declining rate (i.e., a slope of the falling edge of the second reference waveform) may be determined based on the first value, the second value, and the second transition time $T_{fall}$. When the tube voltage is maintained at the low voltage (i.e., the first section 4), the focusing parameter may be maintained at the first value (i.e., the second section 4').

Accordingly, the size of a focus shaped by a focusing device under the focusing parameter changing according to the second reference waveform may be constant and equal to a fixed value when the tube voltage is at the platform stage. The size of the focus may change slightly corresponding to the falling edge and the rising edge of the tube voltage, which may be considered to constant. And the second reference waveform of the focusing parameter may be realized and implemented easily. The focus of radiation rays may be shaped to a fixed value (e.g., 0.5 millimeters×1.0 millimeter) when the tube voltage changes with time according to the first reference waveform of the tube voltage and the focusing parameter changes with time according to the second reference waveform, simultaneously.

Example 3 Exemplary Curves of a Tube Voltage and a Focusing Current Varying with Time FIG. 10 is a diagram illustrating an exemplary waveform of a tube voltage and a waveform of a focusing parameter according to some embodiments of the present disclosure. As shown in FIG. 10, a first waveform of a tube voltage may be periodic. In one cycle, the first waveform of the tube voltage may include a first section 1 (i.e., a rising edge) corresponding to a first transition $T_{rise}$ that it takes for the tube voltage to increase from a low voltage $kV_l$ to a high voltage $kV_h$, a first section 2 corresponding to a fourth time length $T_h$ that the tube voltage is maintained at the high voltage $kV_h$, a first section 3 (i.e., a falling edge) corresponding to a second transition time $T_{fall}$ that it takes for the tube voltage to decrease from the high voltage $kV_h$ to the low voltage $kV_l$, and a first section 4 corresponding to a third time length $T_l$ that the tube voltage maintains at the low voltage $kV_l$.

A second waveform of a focusing parameter (e.g., a focusing current denoted by denoted $I_{coil}$ or a focusing current denoted by denoted $V_{GM}$) may be determined as described according to process 700. The second waveform of the focusing parameter may be periodic. In one cycle, the second waveform of the focusing current or the focusing voltage may include a second section 1" (i.e., a rising edge) corresponding to the first transition $T_{rise}$, a second section 2" corresponding to the fourth time length $T_h$, a second section 3" (i.e., a falling edge) corresponding to the second transition time $T_{fall}$, and a second section 4" corresponding to the third time length $T_l$.

Each value of the focusing parameter may correspond to a value of the tube voltage. The focusing parameter may be determined based on a feedback of the tube voltage according to process 700. The focus of radiation rays may be shaped in a constant value (e.g., 0.5 millimeters×1.0 millimeter) when the tube voltage changes with time according to the first waveform of the tube voltage and the focusing parameter changes with time according to the second waveform, simultaneously.

Figure 11:
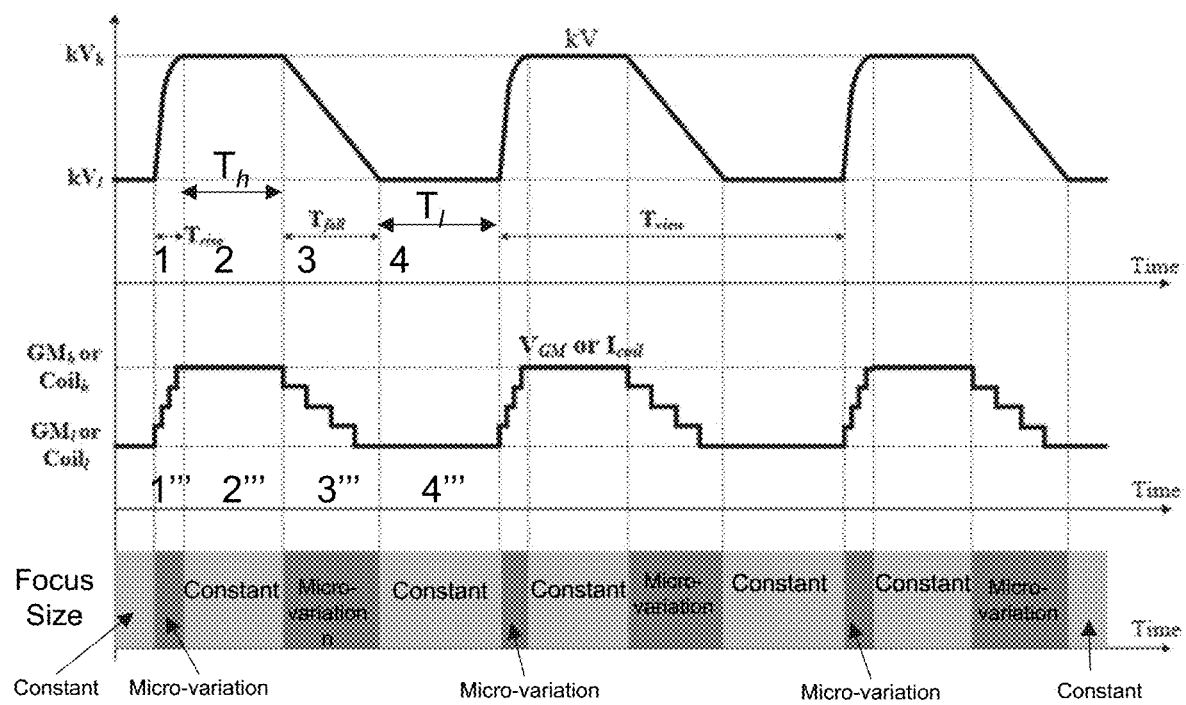
FIG. 11 is a diagram illustrating an exemplary waveform of a tube voltage and a waveform of a focusing parameter according to some embodiments of the present disclosure.

Example 4 Exemplary Curves of a Tube Voltage and a Focusing Current Varying with Time FIG. 11 is a diagram illustrating an exemplary waveform of a tube voltage and a waveform of a focusing parameter according to some embodiments of the present disclosure. As shown in FIG. 11, a first waveform of a tube voltage may be periodic. In one cycle, the first waveform of the tube voltage may include a first section 1 (i.e., a rising edge) corresponding to a first transition $T_{rise}$ that it takes for the tube voltage to increase from a low voltage $kV_l$ to a high voltage $kV_h$, a first section 2 corresponding to a fourth time length $T_h$ that the tube voltage is maintained at the high voltage $kV_h$, a first section 3 (i.e., a falling edge) corresponding to a second transition time $T_{fall}$ that it takes for the tube voltage to decrease from the high voltage $kV_h$ to the low voltage $kV_l$, and a first section 4 corresponding to a third time length $T_l$ that the tube voltage maintains at the low voltage $kV_l$.

A second waveform of a focusing parameter (e.g., a focusing current denoted by denoted $I_{coil}$ or a focusing current denoted by denoted $V_{GM}$) may be determined as described according to process 700. The second waveform of the focusing parameter may be periodic. In one cycle, the second waveform of the focusing current or the focusing voltage may include a second section 1''' (i.e., a rising edge) corresponding to the first transition $T_{rise}$, a second section 2''' corresponding to the fourth time length $T_h$, a second section 3''' (i.e., a falling edge) corresponding to the second transition time $T_{fall}$, and a second section 4''' corresponding to the third time length $T_l$.

Each value of the focusing parameter may correspond to a range of the tube voltage. Feedback values of the tube voltage belonging to a same range of the tube voltage may correspond to a same value of the focusing parameter. For example, if the feedback value of the tube voltage is equal to the high voltage $kV_h$, the value of the focusing parameter may be equal to a maximum value (e.g., $GM_h$ or $Coil_h$). If the feedback value of the tube voltage is equal to the low voltage $kV_l$, the value of the focusing parameter may be equal to a minimum value (e.g., $GM_l$ or $Coil_l$). If the tube voltage changes between the high voltage $kV_h$ and the low voltage $kV_l$ (at the rising edge or falling edge), a range of the tube voltage to which feedback values of the tube voltage belong may be determined. Then the value of the focusing parameter corresponding to the range of the tube voltage may be determined. The focus of radiation rays may be shaped in a constant value (e.g., 0.5 millimeters×1.0 millimeter) when the tube voltage changes with time according to the first waveform of the tube voltage and the focusing parameter changes with time according to the second waveform, simultaneously.

Example 5 Exemplary Curves of a Focusing Voltage Varying with a Tube Voltage

Figure 12:
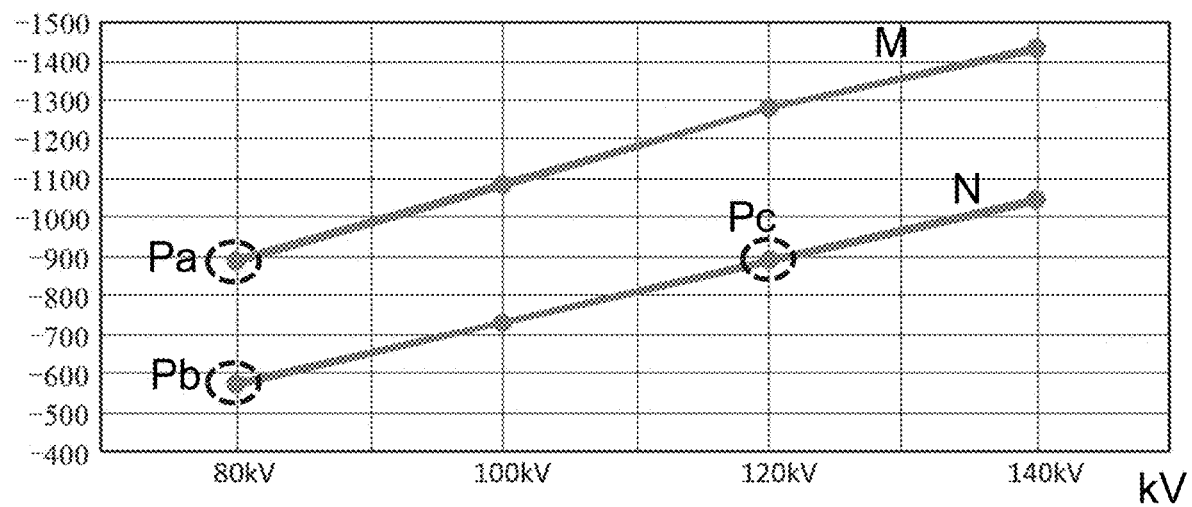
FIG. 12 is a diagram shows exemplary curves of a value of a focusing parameter varying with a tube voltage of a radiation source with respect to different focus sizes according to some embodiments of the present disclosure.

FIG. 12 is a diagram shows exemplary curves of a value of a focusing parameter varying with a tube voltage of a radiation source with respect to different focus sizes according to some embodiments of the present disclosure. As shown in FIG. 12, curve "M" refers to a curve of the average value of a focusing voltage varying with a tube voltage with respect to a focus size of 0.5×1.0 mm², and curve "N" refers to a curve of the average value of a focusing voltage varying with a tube voltage, which corresponds to a focus size of 1.0×1.0 mm².

For a fixed focus size (e.g., 1.0×1.0 mm²), the higher the tube voltage is, the higher the focusing voltage may be. For example, for the curve "N", when the amplitude of the tube voltage is 80 kV (i.e., point Pb), the focusing voltage is about −600 V, and when the amplitude of the tube voltage is 120 kV (i.e., point Pc in FIG. 12), the focusing voltage is about −900 V. For a fixed tube voltage (e.g., 80 kV), the higher the focusing voltage is, the smaller the focus size may be. For example, for the tube voltage as 80 kV, when the focusing voltage is −900 V (i.e., point Pa in FIG. 12), the focus size is 0.5×1.0 mm², and when the focusing voltage is about −600 V (i.e., point Pb in FIG. 12), the focus size is 1.0×1.0 mm². For a fixed focusing voltage (e.g., −900 V), the higher the amplitude of the tube voltage is, the bigger the focus size may be. For example, for the focusing voltage as −900 V, when the amplitude of the tube voltage is 80 kV (i.e., point Pa in FIG. 12), the focus size is 0.5×1.0 mm², and when the amplitude of the tube voltage is about 120 kV (i.e., point Pc in FIG. 12), the focus size is 1.0×1.0 mm².

Figure 13A:
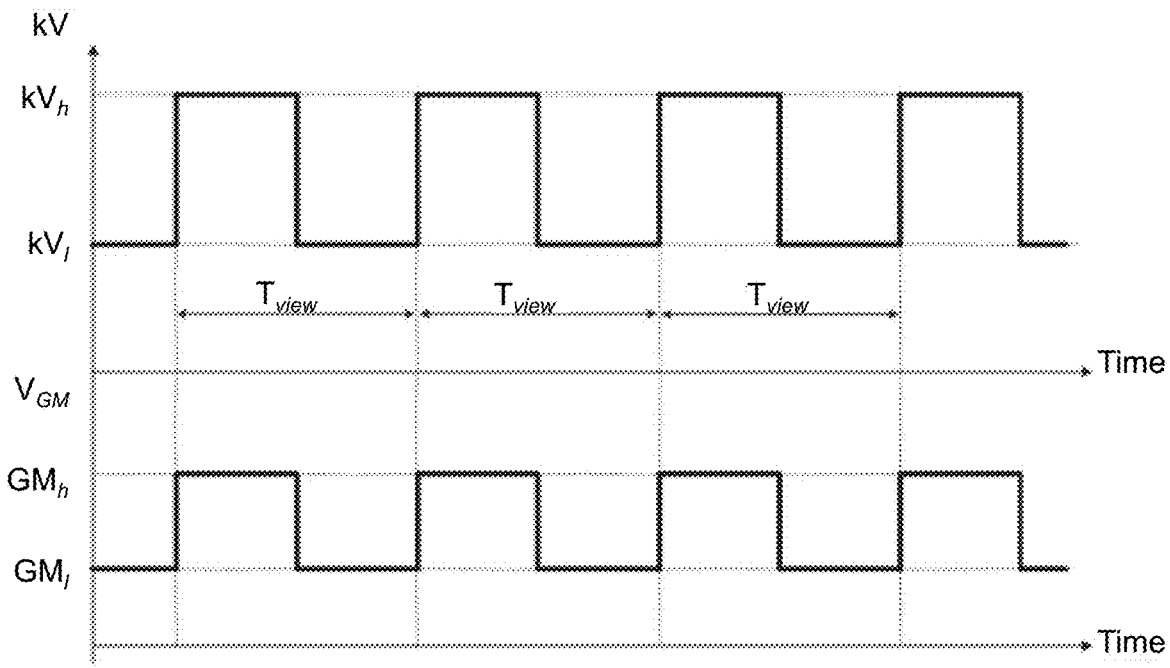
FIGS. 13A and 13B are diagrams illustrating curves of a tube voltage and a focusing parameter varying with time according to some embodiments of the present disclosure.
Figure 13B:
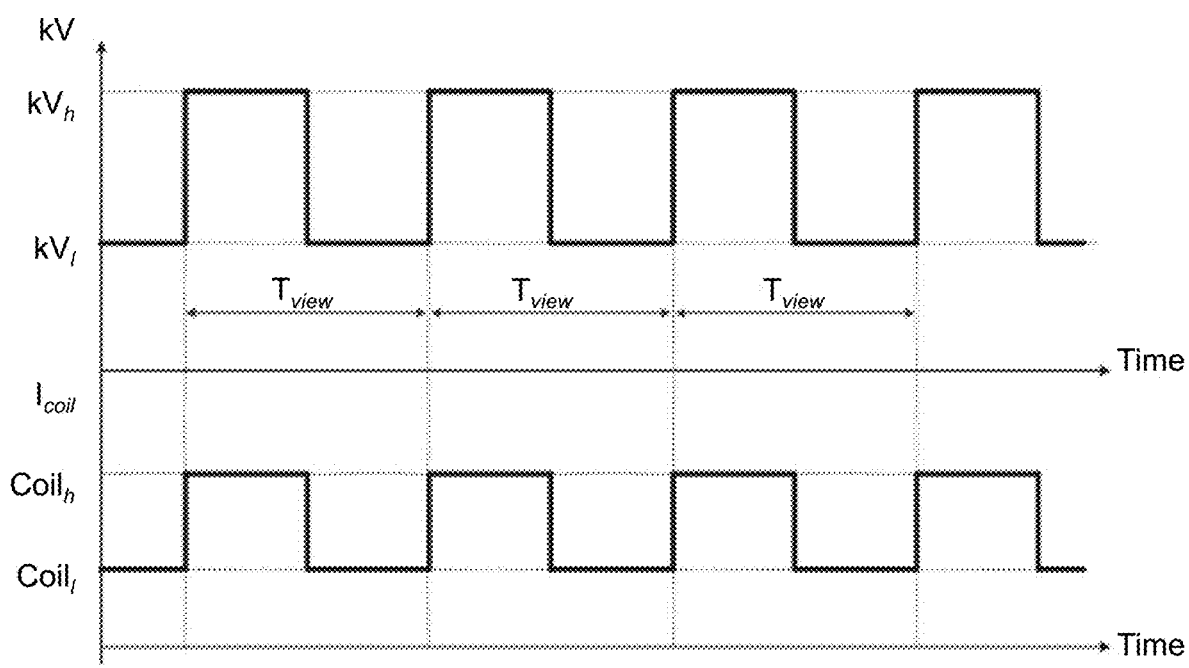

Example 6 Exemplary Curves of a Tube Voltage and a Focusing Current Varying with Time FIGS. 13A and 13B are diagrams illustrating curves of a tube voltage and a focusing parameter varying with time according to some embodiments of the present disclosure. As shown in FIG. 13A, a waveform of a tube voltage is a rectangular waveform. A waveform of a focusing voltage $V_{GM}$ is a rectangular waveform. $GM_h$ is a value of the focusing voltage corresponding to a high voltage $kV_h$. $GM_l$ is a value of the focusing voltage corresponding to a low voltage $kV_l$. The tube voltage switching between the high voltage $kV_h$ and the low voltage $kV_l$ is synchronized with the focusing voltage switching between $GM_h$ and $GM_l$.

As shown in FIG. 13B, a waveform of a tube voltage is a rectangular waveform. A waveform of a focusing current $I_{coil}$ is a rectangular waveform. $Coil_h$ is a value of the focusing voltage corresponding to a high voltage $kV_h$. $Coil_l$ is a value of the focusing voltage corresponding to a low voltage $kV_l$. The tube voltage switching between the high voltage $kV_h$. and the low voltage $kV_l$ is synchronized with the focusing voltage switching between $Coil_h$ and $Coil_l$.

Example 7 Exemplary Curves of a Tube Voltage and a Focusing Parameter Varying with Time FIGS. 14A-14E are diagrams illustrating curves of a tube voltage and a focusing parameter varying with time according to some embodiments of the present disclosure.

Figure 14A:
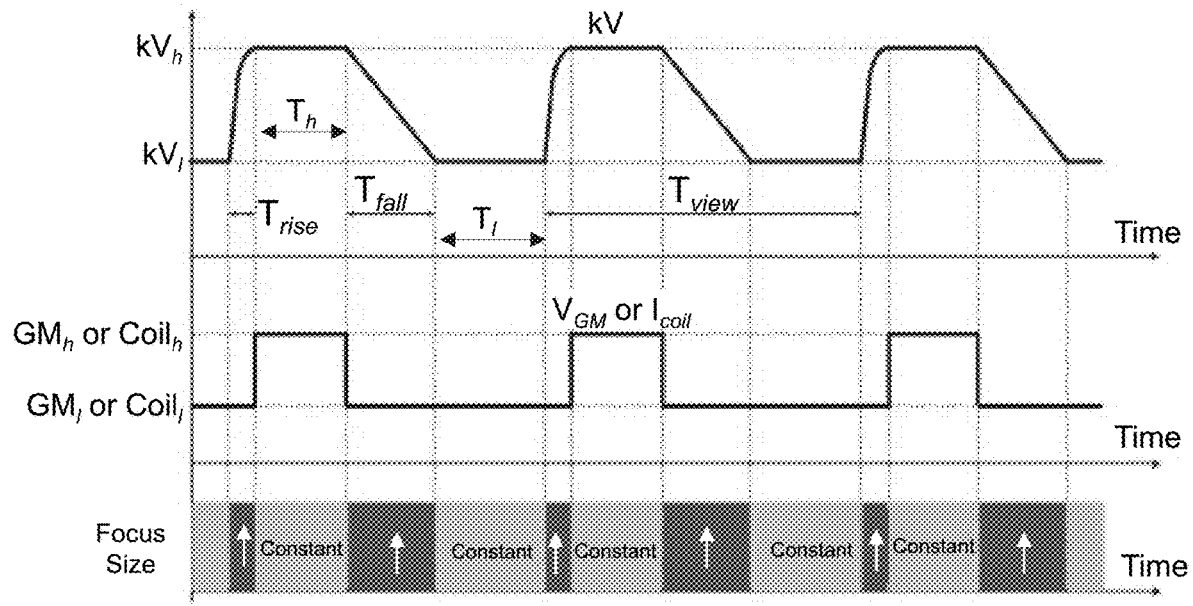
FIGS. 14A-14E are diagrams illustrating curves of a tube voltage and a focusing parameter varying with time according to some embodiments of the present disclosure.

As shown in FIG. 14A, when a tube voltage is maintained at a high voltage $kV_h$ in a platform stage corresponding to a time length $T_h$, a focusing parameter (e.g., a focusing voltage or a focusing current) is equal to a maximum value (e.g., $GM_h$ or $Coil_h$). A size of focus is constant and equal to a fixed value corresponding to the platform stage of the high voltage. When the tube voltage is maintained at a low voltage $kV_l$ in a platform stage corresponding to a time length $T_l$, the focusing parameter (e.g., a focusing voltage or a focusing current) is equal to a minimum value (e.g., $GM_l$ or $Coil_l$). The size of a focus is constant and equal to the fixed value corresponding to the platform stage of the low voltage. When the tube voltage is in a rising edge and a falling edge corresponding to a time length $T_{rise}$ and $T_{fall}$, respectively, the focusing parameter (e.g., a focusing voltage or a focusing current) is equal to the minimum value (e.g., $GM_l$ or $Coil_l$). The size of the focus is variable and exceeds the fixed value corresponding to the platform stage of the low voltage or the high voltage.

Figure 14B:
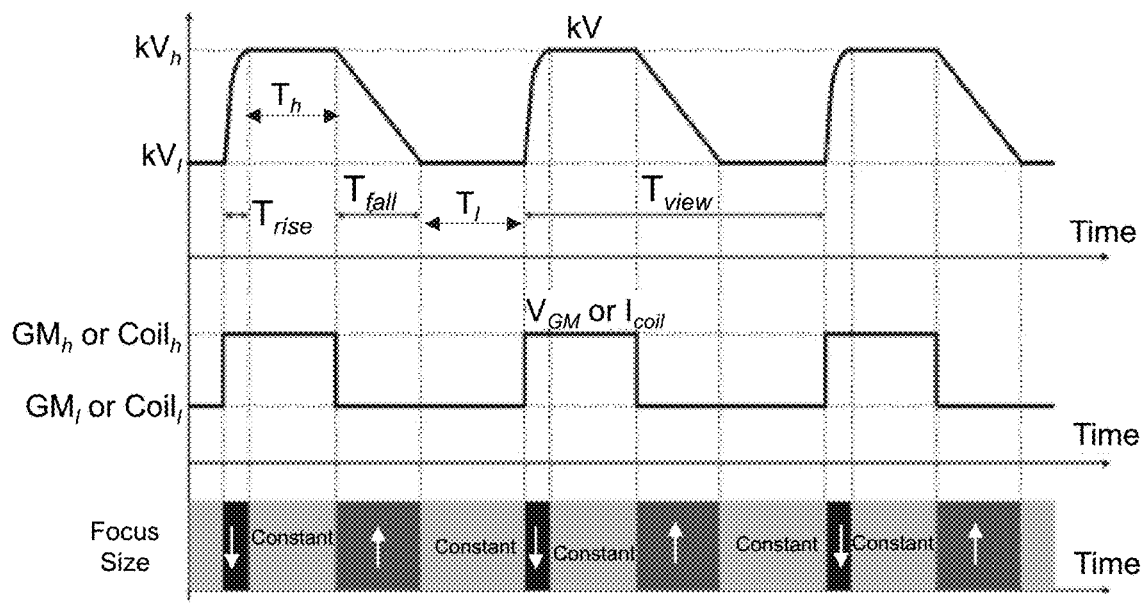

As shown in FIG. 14B, when a tube voltage is maintained at a high voltage $kV_h$ in the platform stage corresponding to the time length $T_h$, a focusing parameter (e.g., a focusing voltage or a focusing current) is equal to a maximum value (e.g., $GM_h$ or $Coil_h$). A size of focus is constant and equal to a fixed value corresponding to the platform stage of the high voltage. When the tube voltage is maintained at a low voltage $kV_l$ in a platform stage corresponding to a time length $T_l$, the focusing parameter (e.g., a focusing voltage or a focusing current) is equal to a minimum value (e.g., $GM_l$ or $Coil_l$). The size of the focus is constant and equal to the fixed value corresponding to the platform stage of the low voltage. When the tube voltage is in a rising edge corresponding to a time length $T_{rise}$, the focusing parameter (e.g., a focusing voltage or a focusing current) is equal to the maximum value (e.g., $GM_h$ or $Coil_h$). The size of the focus is variable and lower than the fixed value corresponding to the platform stage of the high voltage. When the tube voltage is in a falling edge corresponding to a time length $T_{fall}$, the focusing parameter (e.g., a focusing voltage or a focusing current) is equal to the minimum value (e.g., $GM_l$ or $Coil_l$). The size of the focus is variable and exceeds the fixed value corresponding to the platform stage of the low voltage.

Figure 14C:
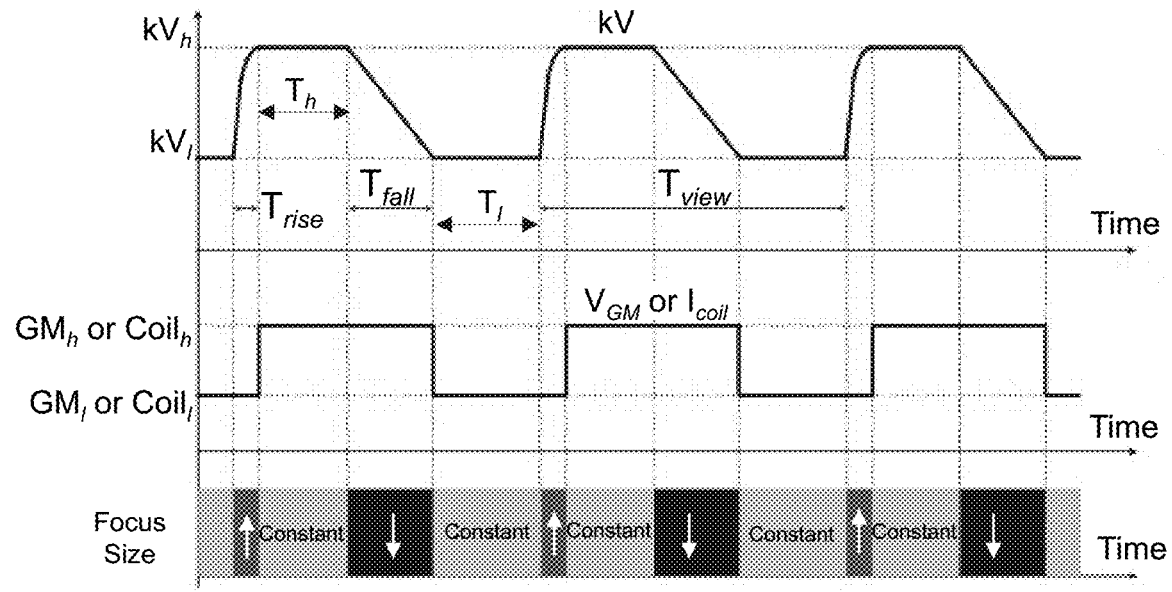

As shown in FIG. 14C, when a tube voltage is maintained at a high voltage $kV_h$ in the platform stage corresponding to the time length $T_h$, a focusing parameter (e.g., a focusing voltage or a focusing current) is equal to a maximum value (e.g., $GM_h$ or $Coil_h$). A size of focus is constant and equal to a fixed value corresponding to the platform stage of the high voltage. When the tube voltage is maintained at a low voltage $kV_l$ in a platform stage corresponding to a time length $T_l$, the focusing parameter (e.g., a focusing voltage or a focusing current) is equal to a minimum value (e.g., $GM_l$ or $Coil_l$). The size of the focus is constant and equal to the fixed value corresponding to the platform stage of the low voltage. When the tube voltage is in a rising edge corresponding to a time length $T_{rise}$, the focusing parameter (e.g., a focusing voltage or a focusing current) is equal to the minimum value (e.g., $GM_l$ or $Coil_l$). The size of the focus is variable and exceeds the fixed value corresponding to the platform stage of the high voltage. When the tube voltage is in a falling edge corresponding to a time length $T_{fall}$, the focusing parameter (e.g., a focusing voltage or a focusing current) is equal to the maximum value (e.g., $GM_h$ or $Coil_h$). The size of the focus is variable and lower than the fixed value corresponding to the platform stage of the low voltage.

Figure 14D:
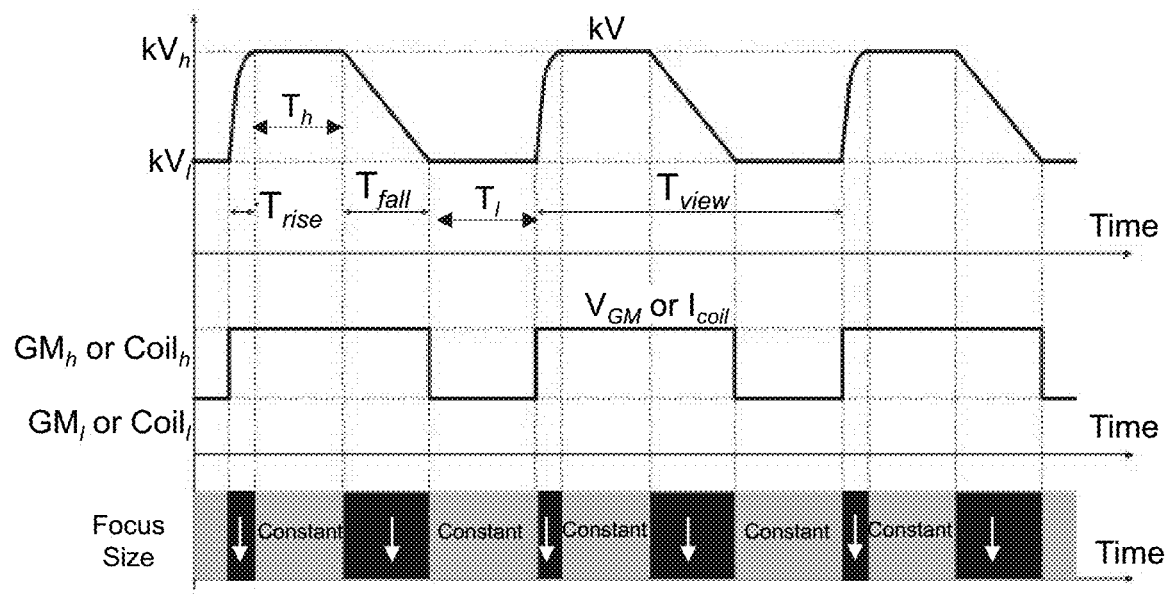

As shown in FIG. 14D, when a tube voltage is maintained at a high voltage $kV_h$ in a platform stage corresponding to a time length $T_h$, a focusing parameter (e.g., a focusing voltage or a focusing current) is equal to a maximum value (e.g., $GM_h$ or $Coil_h$). A size of focus is constant and equal to a fixed value corresponding to the platform stage of the high voltage. When the tube voltage is maintained at a low voltage $kV_l$ in a platform stage corresponding to a time length $T_l$, the focusing parameter (e.g., a focusing voltage or a focusing current) is equal to a minimum value (e.g., $GM_l$ or $Coil_l$). The size of the focus is constant and equal to the fixed value corresponding to the platform stage of the low voltage. When the tube voltage is in a rising edge and a falling edge corresponding to a time length $T_{rise}$ and $T_{fall}$, respectively, the focusing parameter (e.g., a focusing voltage or a focusing current) is equal to the maximum value (e.g., $GM_h$ or $Coil_h$). The size of the focus is variable and lower than the fixed value corresponding to the platform stage of the low voltage or the high voltage.

Figure 14E:
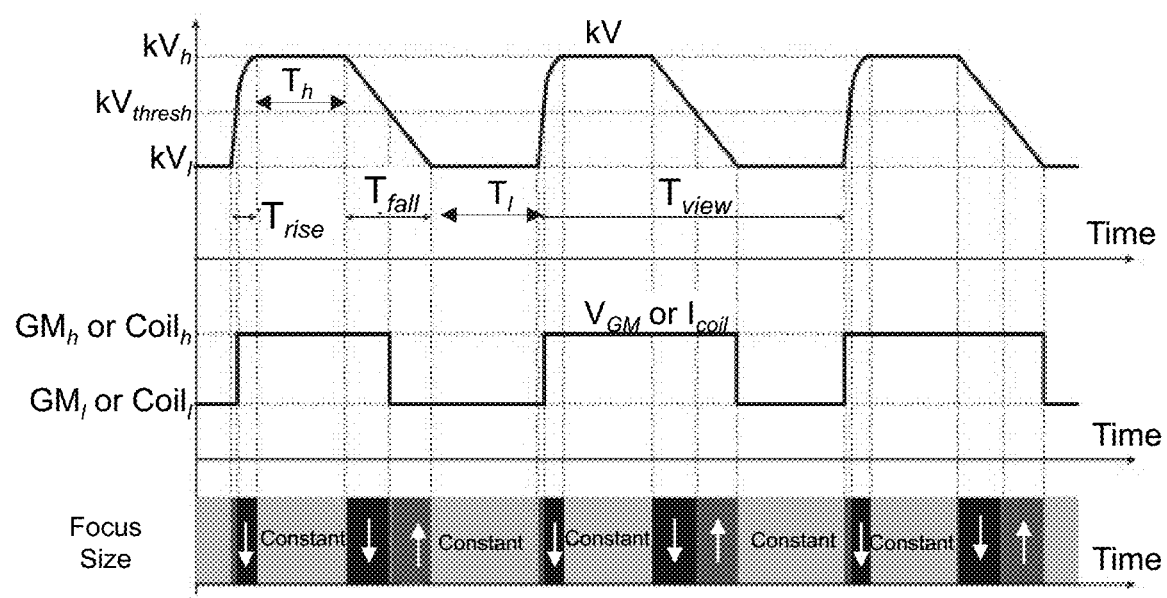

As shown in FIG. 14E, when a tube voltage is maintained at a high voltage $kV_h$ in a platform stage corresponding to a time length $T_h$, a focusing parameter (e.g., a focusing voltage or a focusing current) is equal to a maximum value (e.g., $GM_h$ or $Coil_h$). A size of focus is constant and equal to a fixed value corresponding to the platform stage of the high voltage. When the tube voltage is maintained at a low voltage $kV_l$ in a platform stage corresponding to a time length $T_l$, the focusing parameter (e.g., a focusing voltage or a focusing current) is equal to a minimum value (e.g., $GM_l$ or $Coil_l$). The size of the focus is constant and equal to the fixed value corresponding to the platform stage of the low voltage. When the tube voltage is in a rising edge and a falling edge corresponding to a time length $T_{rise}$ and $T_{fall}$, respectively, if the tube voltage exceeds a voltage threshold $kV_{threshold}$, the focusing parameter (e.g., a focusing voltage or a focusing current) is equal to the maximum value (e.g., $GM_h$ or $Coil_h$). If the tube voltage is lower than the voltage threshold $kV_{threshold}$, the focusing parameter (e.g., a focusing voltage or a focusing current) is equal to the maximum value (e.g., $GM_h$ or $Coil_h$). The size of the focus is variable corresponding to the falling edge and the rising edge. The size of the focus corresponding to a portion of each of the falling edge and rising edge of the tube voltage is lower than the fixed value. The size of the focus corresponding to the rest portion of each of the falling edge and rising edge of the tube voltage exceeds the fixed value.

According to FIGS. 14A-14E, the size of the focus may be variable corresponding to the falling edge and the rising edge of the tube voltage. A change of the size of the focus corresponding to the falling edge and the rising edge of the tube voltage may be great which may influence a spatial resolution of an image. And the size of the focus may be lower than a desired value which may cause an area or region of an anode target of a tube overheating and damage the tube.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
   at least one storage device storing executable instructions, and
   at least one processor in communication with the at least one storage device,
   when executing the executable instructions, causing the system to perform operations including:
      obtaining a feedback of a tube voltage applied to an x-ray radiation source of an x-ray radiation device for generating x-ray radiation rays; and
      determining, based on the feedback of the tube voltage, a specific value of a focusing parameter associated with a focusing device of the x-ray radiation device, wherein the focusing parameter includes at least one of a focusing voltage or a focusing current;
      causing the focusing device to shape a focus of the x-ray radiation rays according to the determined value of the focusing parameter, wherein the focus of the x-ray radiation rays satisfies an operational constraint under the specific value of the focusing parameter.

2. The system of claim 1, wherein the at least one processor is further configured to cause the system to perform the operations including:
   obtaining projection data generated by detecting at least a portion of the x-ray radiation rays by a detector of the x-ray radiation device; and
   generating, based on the projection data, one or more images using an energy imaging technique.

3. The system of claim 2, wherein a sampling speed of the feedback of the tube voltage is lower than a sampling speed of the projection data.

4. The system of claim 1, wherein the operational constraint includes that a size of the focus of the x-ray radiation rays is in a range when the tube voltage changes according to a reference waveform.

5. The system of claim 1, wherein the operational constraint includes that a size of the focus of the x-ray radiation rays is equal to a fixed value when the tube voltage changes according to a reference waveform.

6. The system of claim 1, wherein the focusing parameter is the focusing voltage, the focusing device is configured to shape the focus of the x-ray radiation rays by generating an electric field under the focusing voltage.

7. The system of claim 1, wherein the focusing parameter is the focusing current, the focusing device is configured to shape the focus of the x-ray radiation rays by generating a magnetic field under the focusing current.

8. The system of claim 1, wherein the feedback of the tube voltage includes at least one of a value of the tube voltage or a current time point when the value of the tube voltage is obtained.

9. The system of claim 8, wherein to determine, based on the feedback of the tube voltage, a specific value of a focusing parameter associated with a focusing device, the at least one processor is further configured to cause the system to perform the operations including:
   obtaining a relationship between the tube voltage and the focusing parameter with respect to a specific size of the focus; and
   determining, based on the relationship, the specific value of the focusing parameter corresponding to the value of the tube voltage.

10. The system of claim 9, wherein the relationship between the tube voltage and the focusing parameter includes a first portion corresponding to a rising edge that the tube voltage increases from a first voltage to a second voltage and a second portion corresponding to a falling edge that the tube voltage decreases from the second voltage to the first voltage.

11. The system of claim 10, wherein to determine, based on the relationship, the specific value of the focusing parameter corresponding to the value of the tube voltage, the at least one processor is further configured to cause the system to perform the operations including:
   determining whether the value of the tube voltage belongs to the falling edge or the rising edge; and
   determining, based on a determined result and the relationship between the tube voltage and the focusing parameter, the specific value of the focusing parameter corresponding to the value of the tube voltage.

12. The system of claim 11, wherein to determine whether the value of the tube voltage belongs to the falling edge or the rising edge, the at least one processor is further configured to cause the system to perform the operations including:
   determining a changing rate of the tube voltage between the current time point and a last time point before the current time point based on a relationship between the tube voltage and time with respect to a specific size of the focus; and
   determining, based on the changing rate of the tube voltage, whether the value of the tube voltage belongs to the falling edge or the rising edge.

13. The system of claim 12, wherein the relationship between the tube voltage and the focusing parameter further includes multiple groups of values of the tube voltage and the focusing parameter, each group including a value of the tube voltage and a corresponding value of the focusing parameter.

14. The system of claim 12, wherein the relationship between the tube voltage and the focusing parameter includes multiple groups of ranges of the tube voltage and values of the focusing parameter, each group including a range of the tube voltage and a corresponding value of the focusing parameter.

15. The system of claim 14, wherein to determine, based on the relationship, the specific value of the focusing parameter corresponding to the value of the tube voltage, the at least one processor is further configured to cause the system to perform the operations including:
   determining a specific range of the tube voltage where the value belongs to; and
   determining, based on the changing rate of the tube voltage, the relationship, and the specific range of the tube voltage, the specific value of the focusing parameter corresponding to the feedback of the tube voltage.

16. The system of claim 8, wherein to determine, based on the feedback of the tube voltage, a specific value of a focusing parameter associated with a focusing device, the at least one processor is further configured to cause the system to perform the operations including:
   obtaining a relationship between the focusing parameter and time with respect to a specific size of the focus; and determining, based on the relationship and the current time point when the value of the tube voltage is obtained, the specific value of the focusing parameter corresponding to the feedback of the tube voltage.

17. The system of claim 16, wherein to obtain a relationship between the focusing parameter and time with respect to a specific size of the focus, the at least one processor is further configured to cause the system to perform the operations including:

determining, based at least in part on a first time length that it takes for the focusing parameter to change from a minimum value to a maximum value when the tube voltage switches from a first voltage to a second voltage within the first time length, a first changing rate of the focusing parameter changing from the minimum value to the maximum value;

determining, based at least in part on a second time length that it takes for the focusing parameter to change from the maximum value to the minimum value when the tube voltage switches from the second voltage to the first voltage within the second time length, a second changing rate of the focusing parameter changing from the maximum value to the minimum value; and determining, based at least in part on the first changing rate or the second changing rate, the relationship between the focusing parameter and time.

18. A method implemented on a computing device having at least one processor and at least one storage device, the method comprising:

obtaining a feedback of a tube voltage applied to an x-ray radiation source of an x-ray radiation device for generating x-ray radiation rays;

determining, based on the feedback of the tube voltage, a specific value of a focusing parameter associated with a focusing device of the x-ray radiation device, wherein the focusing parameter includes at least one of a focusing voltage or a focusing current; and causing the focusing device to shape a focus of the x-ray radiation rays according to the determined value of the focusing parameter, wherein the focus of the x-ray radiation rays satisfies an operational constraint under the specific value of the focusing parameter.

19. The method of claim 18, further comprising:

generating, based on at least a portion of the x-ray radiation rays detected by a detector of the x-ray radiation device, one or more images using an energy imaging technique.

20. A non-transitory computer readable medium, comprising a set of instructions, wherein when executed by at least one processor, the set of instructions direct the at least one processor to effectuate a method, the method comprising:

obtaining a feedback of a tube voltage applied to an x-ray radiation source of an x-ray radiation device for generating x-ray radiation rays;

determining, based on the feedback of the tube voltage, a specific value of a focusing parameter associated with a focusing device of the x-ray radiation device, wherein the focusing parameter includes at least one of a focusing voltage or a focusing current; and causing the focusing device to shape a focus of the x-ray radiation rays according to the determined value of the focusing parameter, wherein the focus of the x-ray radiation rays satisfies an operational constraint under the specific value of the focusing parameter.

* * * * *